(12) United States Patent
Meng

(10) Patent No.: US 8,642,636 B2
(45) Date of Patent: Feb. 4, 2014

(54) DIMERIC 1-ARYLPYRAZOLE DERIVATIVES FOR USE AGAINST ECTOPARASITES, AGRICULTURAL PESTS, AND HOUSEHOLD PESTS

(75) Inventor: Charles Q. Meng, Johns Creek, GA (US)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 13/129,031

(22) PCT Filed: Nov. 18, 2009

(86) PCT No.: PCT/US2009/064981
§ 371 (c)(1),
(2), (4) Date: Jun. 17, 2011

(87) PCT Pub. No.: WO2010/059719
PCT Pub. Date: May 27, 2010

(65) Prior Publication Data
US 2011/0245157 A1    Oct. 6, 2011

Related U.S. Application Data

(60) Provisional application No. 61/116,021, filed on Nov. 19, 2008.

(51) Int. Cl.
    *A01N 43/56*    (2006.01)
(52) U.S. Cl.
    USPC ........... 514/404; 514/406; 514/407; 514/183; 514/918; 514/740
(58) Field of Classification Search
    None
    See application file for complete search history.

(56) References Cited

U.S. PATENT DOCUMENTS

| | | | |
|---|---|---|---|
| 3,966,900 A | 6/1976 | Hennart et al. | 424/27 |
| 2002/0111352 A1* | 8/2002 | Huber et al. | 514/229.2 |
| 2004/0167175 A1* | 8/2004 | Soll et al. | 514/341 |
| 2007/0275976 A1 | 11/2007 | Schnatterer et al. | 514/252.11 |

FOREIGN PATENT DOCUMENTS

WO    WO 2006/000313 A1 *    1/2006 ........... C07D 231/44

OTHER PUBLICATIONS

"Chapter 15: Identical and Nonidentical Twin Drugs" J. Bourguignon, Practice of Medicinal Chemistry, Academic Press Limited (Jan. 1, 1996), pp. 261-293.*

"Structural variations in nickel(II) and copper(II) $MN_4$ Schiff-base complexes with deprotonated tetradentate N,N'-bis(5-aminopyrazol-4-ylmethylene)polymethylenediamine ligands", Alexander L. Nivorozhkin et al., *J. Chem. Soc., Dalton Trans.*, 1996, vol. 7, pp. 1215-1221.

"A facile synthesis of 3,5-dialyl/diaryl-4-aryl-8-(4-methylphenyl)-1,7-diphenyl-1H,4H,7H,8H-dipyrazolo-[3,4- b:4',3'-e]pyridines",V. K. Ahluwalia et al., *Indian J. Chem.*, Nov. 1997, vol. 36B, pp. 1059-1061.

(Continued)

*Primary Examiner* — Cecilia J Tsang
*Assistant Examiner* — Randall L Beane
(74) *Attorney, Agent, or Firm* — Judy Jarecki-Black; John Ezcurra; Merial Limited

(57) ABSTRACT

This invention provides for dimeric1-arylpyrazole compounds, of formulas (I), (II), and (III):

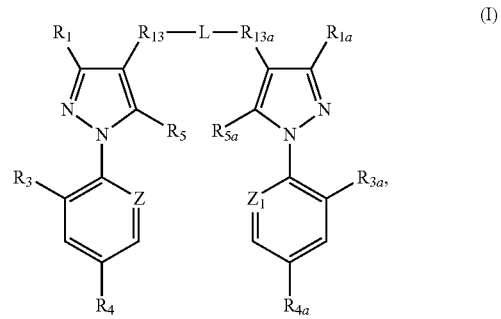

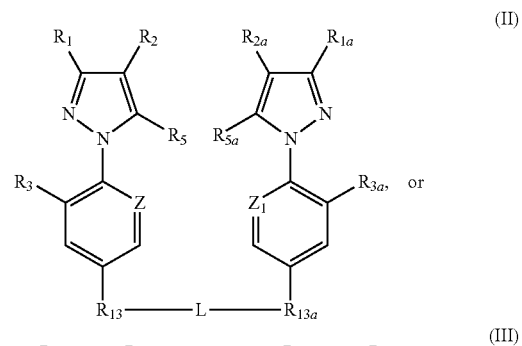

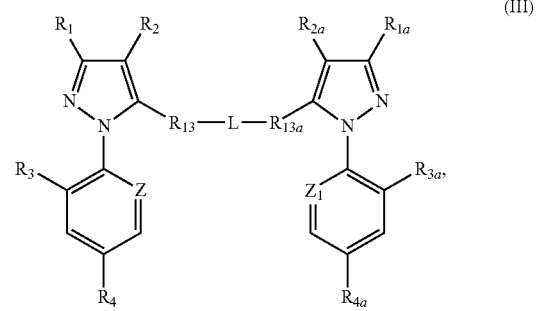

or salts thereof, and the use of these compounds against ectoparasites such as insects, arthropods and acarina. The resulting compounds may be used in veterinary formulations such as, for example, spot-on and pour-on formulations, which may be used for treatment, controlling and preventing of parasitic infections in warm-blooded animals and birds.

14 Claims, No Drawings

(56) References Cited

OTHER PUBLICATIONS

"Nickel(II) $N_2O_2$ Schiff-base complexes incorporating pyrazole: syntheses, characterization and acidity of the metal centre towards co-ordinating", Agnete la Cour et al., *J. Chem. Soc., Dalton Trans.*, 1996, vol. 7, pp. 3437-3447.

"The preparation of some pyrazole derivatives" I.L. Finar and G.H. Lord, *J. Chem. Soc.*, 1959, pp. 1819-1821.
"*Chapter 15: Identical and Nonidentical Twin Drugs*" Jean-Jaques Bourguignon, the Practice of Medicinal Chemistry, Academic Press Limited, Jan. 1, 1996, pp. 261-293.

\* cited by examiner

DIMERIC 1-ARYLPYRAZOLE DERIVATIVES FOR USE AGAINST ECTOPARASITES, AGRICULTURAL PESTS, AND HOUSEHOLD PESTS

CROSS REFERENCE TO RELATED APPLICATIONS

This application is a U.S. national stage application of International Patent Application No. PCT/US09/64981, filed Nov. 18, 2009, which claims the benefit of priority to U.S. Provisional Patent Application No. 61/116,021, filed Nov. 19, 2008, which is incorporated herein by reference in its entirety.

FIELD OF THE INVENTION

The present invention relates to dimeric 1-arylpyrazole compounds of general formula:

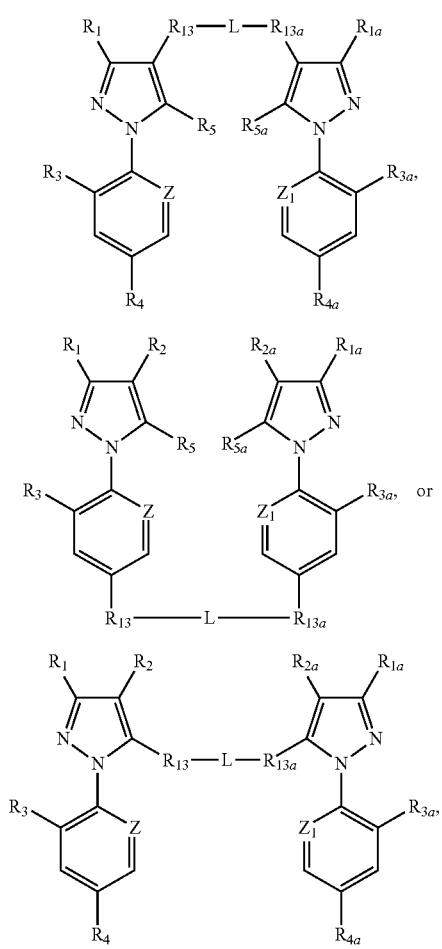

wherein: $R_1$, $R_{1a}$, $R_2$, $R_{2a}$, $R_3$, $R_{3a}$, $R_4$, $R_{4a}$, $R_5$, $R_{5a}$, $R_{13}$, $R_{13a}$, L, Z, $Z_1$ and n are as defined below, or salts thereof, and the use of these compounds against ectoparasites (including insects and acarids).

BACKGROUND OF THE INVENTION

Animals such as mammals and birds are often susceptible to parasite infestations. These parasites may be ectoparasites such as insects, and endoparasites such as filariae and worms.

Domesticated animals, such as cats and dogs, are often infested with one or more of the following ectoparasites:
- fleas (*Ctenocephalides felis, Ctenocephalides* sp. and the like),
- ticks (*Rhipicephalus* sp., *Ixodes* sp., *Dermacentor* sp., *Amblyomma* sp. and the like),
- mites (*Demodex* sp., *Sarcoptes* sp., *Otodectes* sp. and the like),
- lice (*Trichodectes* sp., *Cheyletiella* sp., *Linognathus* sp., and the like), and
- flies (*Hematobia* sp., *Musca* sp., *Stomoxys* sp., *Dermatobia* sp., *Cochliomyia* sp.,
- mosquitoes (family Culicidae), and the like.

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*), and may also transmit pathogens to humans.

Similarly, ticks are also harmful to the physical and psychological health of the animal or human. However, the most serious problem associated with ticks is that they are the vector of pathogenic agents, which cause diseases in both humans and animals Major diseases which are caused by ticks include borreliosis (Lyme disease caused by *Borrelia burgdorferi*), babesiosis (or piroplasmosis caused by *Babesia* sp.) and rickettsiosis (also known as Rocky Mountain spotted fever). Ticks also release toxins which cause inflammation or paralysis in the host. Occasionally, these toxins are fatal to the host, such as in the case of the Australian paralysis tick, *Ixodes holocyclus*.

Moreover, mites and lice are particularly difficult to combat since there are very few active substances which act on these parasites and they require frequent treatment.

Likewise, farm animals are also susceptible to parasite infestations. For example, cattle are affected by a large number of parasites. Likewise, arthropod pests, such as fleas, lice and ticks, and mites infest poultry. A parasite that is very prevalent among farm animals is the tick genus *Boophilus*, especially those of the species *microplus* (cattle tick), *decoloratus* and *anulatus*. Ticks, such as *Boophilus microplus*, are particularly difficult to control because they live in the pasture where the farm animals graze. Other important parasites of cattle and sheep are listed as follows in order of decreasing importance:

(a) myiases-causing flies such as *Dermatobia hominis* (known as Berne in Brazil), Hypoderma, and *Cochlyomia hominivorax* (greenbottle); sheep myiases-causing flies such as *Lucilia sericata, Lucilia cuprina* (known as blowfly strike in Australia, New Zealand and South Africa). These are flies whose larva constitutes the animal parasite;

(b) flies proper, namely those whose adult constitutes the parasite, such as *Haematobia irritans* (horn fly);

(c) lice such as *Linognathus vituli* etc.; and (d) mites such as *Sarcoptes scabiei* and *Psoroptes ovis*.

The compounds of the invention may also be useful against household pests including, but not limited to, cockroach, *Blatella* sp., clothes moth, *Tineola* sp., carpet beetle, *Attagenus* sp. and the housefly *Musca domestica* and against *Solenopsis invicta* (imported fire ants), termites, and the like.

These compounds may further be useful against agricultural pests such as aphids (*Acyrthiosiphon* sp.), locusts, and boll weevils as well as against insect pests that attack stored grains, such as *Tribolium* sp., and against immature stages of insects living on plant tissue.

The above list is not exhaustive and other ectoparasites are well known in the art to be harmful to animals, humans and crops.

Compounds that exhibit a degree of activity against a wide range of ectoparasites including arthopods and insects are known in the art. One such class of compounds is the arylpyrazoles which are referred to, for example, in U.S. Pat. Nos. 4,963,575; 5,232,940; 5,547,974; 5,608,077; 5,714,191; 5,817,688; 5,885,607; 5,916,618; 5,922,885; 5,965,491; 5,994,386; 6,010,710; 6,069,157; 6,083,519; 6,096,329; 6,124,339; 6,160,002; 6,180,798; 6,350,771; 6,372,774; 6,395,906; 6,531,501; 6,630,499; 6,685,954; 7,067,548; and U.S. application Ser. No. 11/825,050, all of which are incorporated herein by reference in their entirety. Arylpyrazoles are also referred to, for example, in EP 0 234 119, EP 0 295 117, EP 0 352 944; EP 0 780 378; EP 0 846 686; and EP 0 948 485, all of which are incorporeated herein by reference.

The arylpyrazoles are known to possess excellent activity against insects, such as fleas and ticks. Fipronil is a specific type of 1-N-arylpyrazole that is particularly effective against fleas and ticks and is the active ingredient in Frontline® and Frontline Plus®.

Bis-1-arylpyrazoles containing a disulfide linkage at the 4-position of the pyrazole are used as synthetic intermediates en route to monomeric 1-arylpyrazoles in EP 0 295 117, however these derivatives themselves are not disclosed as pesticidal agents therein. Bis-N-phenylpyrazole derivatives linked through the 5-position of the pyrazole are described in U.S. application Ser. No. 11/615,668.

However, ectoparasiticidal agents can vary in their effectiveness to a particular parasite as well as vary in their cost of production. Moreover, the results of ectoparasiticidal agents may not always be satisfactory because of, for example, the development of resistance by the parasite to the therapeutic agent, as is the case, for example, with carbamates, organophosphorus compounds and pyrethroids. In conjunction with developing resistance issues, modern pesticidal research must also consider spectrum of action, side effect profiles with respect to animal hosts, and convenience of dosing regimen.

Thus, there remains a need in the art for more effective and rapidly acting novel antiparasitic compositions for the treatment and protection of animals, e.g. mammals, fish and birds, from a wide range of parasites. There is a need in the art for an antiparasitic formulation which is easy to use on any type of domestic animal, irrespective of its size and the nature of its coat and which does not require administration over the entire body of the mammal, fish or bird. Further, the formulation should be of prolonged efficacy thereby reducing the number of applications.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby explicitly incorporated herein by reference, and may be employed in the practice of the invention.

Citation or identification of any document in this application is not an admission that such document is available as prior art to the present invention.

SUMMARY OF THE INVENTION

The invention provides, and it is an object of the invention to provide, novel compounds, compositions and uses thereof for the treatment or prophylaxis of parasites of animals (either wild or domesticated), e.g., livestock and companion animals such as cats, dogs, horses, chickens, sheep, goats, pigs, turkeys and cattle, with the aim of ridding these hosts of parasites commonly encountered by such animals.

The invention also provides for effective and long lasting destruction of ectoparasites, such as fleas, ticks, mites, mosquitoes, flies and lice. The invention may also be effective against endoparasites, cestodes, nematodes, such as filariae, and roundworms of the digestive tract of animals and humans.

The dimeric 1-arylpyrazole compounds of the invention, alone or in combination, may be able to provide protection against ectoparasites which may include speed of efficacy, long lasting efficacy (e.g. for a period of at least one month), enhanced efficacy, and enhanced selectivity.

One aspect of the invention is to provide (1) a dimeric 1-arylpyrazole compound of formula (I):

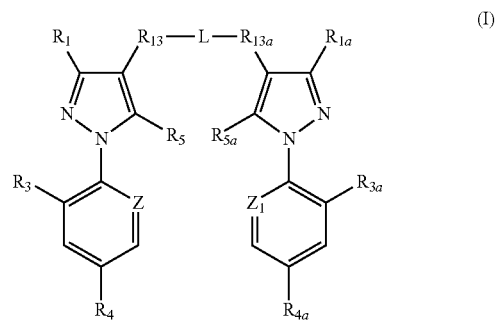

(I)

wherein:

$R_1$ and $R_{1a}$ are independently selected from the group consisting of hydrogen, cyano, halogen, $R_6$, —C(=O)$R_6$, —C(=O)$R_8$, —C(=O)NR$_{11}$R$_{12}$, —CH(=NR$_7$), —CH(=NR$_8$), —C(=NR$_7$)R$_7$, —C(=NR$_7$)R$_8$, —C(=NR$_8$)R$_7$, —C(=NNR$_7$)R$_7$, —C(=NNR$_7$)R$_8$, —C(=NNR$_8$)R$_7$, and —C(S)NR$_7$R$_{11}$;

$R_3$ and $R_{3a}$ are independently selected from the group consisting of hydrogen, halogen, cyano, nitro, alkyl, cycloalkyl, haloalkyl, alkoxy, and haloalkoxy;

$R_4$ and $R_{4a}$ are independently selected from the group consisting of halogen, cyano, nitro, $R_7$, $R_8$, —C(O)R$_{11}$, —C(=O)NR$_{11}$R$_{12}$, —C(=NR$_7$)R$_7$, —C(=NR$_7$)R$_8$, —C(=NR$_7$)NR$_{11}$R$_{12}$, —S(O)$_n$R$_{11}$, and SF$_5$;

$R_5$ and $R_{5a}$ are independently selected from the group consisting of $R_{10}$, $R_{11}$, —C(=NR$_7$)R$_7$, —C(=NR$_7$)R$_8$, —C(=NR$_8$)R$_7$, —C(=NR$_7$)NR$_{11}$R$_{12}$, —C(=S)NR$_{11}$R$_{12}$, —NR$_{11}$R$_{12}$, —NR$_{11}$C(=O)R$_8$, —NR$_{11}$C(=O)R$_{11}$, and —N=C(R$_{11}$)NR$_6$;

Z and $Z_1$ are independently selected from the group consisting of a nitrogen atom and C—R$_3$;

$R_6$ is selected from the group consisting of alkyl, haloalkyl, cycloalkyl, halocycloalkyl, alkenyl, alkynyl, aryl and heteroaryl,
wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and $R_6$;

$R_8$ is selected from the group consisting of —OR$_9$, —OR$_{11}$, —SR$_9$, —SR$_{11}$, —NR$_9$R$_{11}$, and —NR$_{11}$R$_{12}$;

$R_9$ is selected from the group consisting of aryl and heteroaryl,
wherein said aryl and heteroaryl groups are optionally substituted with one or more groups independently selected from the group consisting of $R_{10}$ and $R_{11}$;

R$_{10}$ is selected from the group consisting of cyano, nitro, hydroxyl, halogen, alkyl, cycloalkyl, haloalkyl, alkoxy, haloalkoxy, —S(O)—R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)—R$_{11}$, —NR$_{11}$S(O)—NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

R$_{11}$ and R$_{12}$ are independently selected from the group consisting of hydrogen, alkyl, haloalkyl, cycloalkyl, halocycloalkyl, alkenyl, haloalkenyl, alkynyl, and haloalkynyl;

R$_{13}$ and R$_{13a}$ are independently selected from the group consisting of a bond, —O—, —NR$_{11}$—, —NR$_{11}$C(=O)—, —NR$_{11}$C(=S)—, —NR$_{11}$C(=O)O—, —NR$_{11}$C(=O)NR$_{11}$—, —NR$_{11}$C(=S)NR$_{11}$—, —NR$_{11}$SO$_2$NR$_{11}$—, —NR$_{11}$SO$_2$—, —C(=NR$_7$)—, —C(=NR$_8$)—, —C(=O)—, —C(=O)NR$_{11}$—, —C(=S)NR$_{11}$—, —S(O)$_n$—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or (2) a salt thereof.

A second aspect of the invention is to provide (1) a dimeric 1-arylpyrazole compound of formula (II):

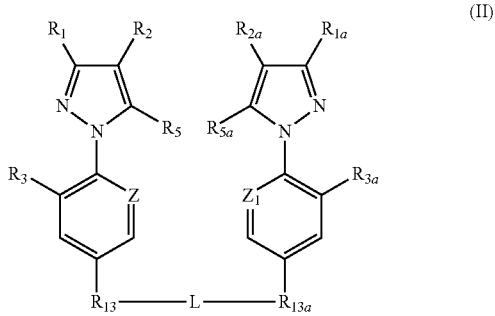

(II)

wherein:

R$_1$ and R$_{1a}$ are independently selected from the group consisting of hydrogen, cyano, halogen, R$_6$, —C(=O)R$_6$, —C(=O)R$_8$, —C(=O)NR$_{11}$R$_{12}$, —CH(=NR$_7$), —CH(=NR$_8$), —C(=NR$_7$)R$_7$, —C(=NR$_7$)R$_8$, —C(=NR$_8$)R$_7$, —C(=NNR$_7$)R$_7$, —C(=NNR$_7$)R$_8$, —C(=NNR$_8$)R$_7$, and —C(S)NR$_7$R$_{11}$;

R$_2$ and R$_{2a}$ are independently selected from the group consisting of S(O)$_n$R$_{11}$, and 4,5-dicyanoimidazol-2-yl;

R$_3$ and R$_{3a}$ are independently selected from the group consisting of hydrogen, halogen, cyano, nitro, alkyl, cycloalkyl, haloalkyl, alkoxy, and haloalkoxy;

R$_5$ and R$_{5a}$ are independently selected from the group consisting of R$_{10}$, R$_{11}$, —C(=NR$_7$)R$_7$, —C(=NR$_7$)R$_8$, —C(=NR$_8$)R$_7$, —C(=NR$_7$)NR$_{11}$R$_{12}$, —C(=S)NR$_{11}$R$_{12}$, —NR$_{11}$R$_{12}$, —NR$_{11}$C(=O)R$_8$, —NR$_{11}$C(=O)R$_{11}$, and —N=C(R$_{11}$)NR$_6$;

Z and Z$_1$ are independently selected from the group consisting of a nitrogen atom and C—R$_3$;

R$_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of R$_8$, R$_9$ and R$_{10}$;

R$_7$ is selected from the group consisting of H and R$_6$;

R$_8$ is selected from the group consisting of —OR$_9$, —OR$_{11}$, —SR$_9$, —SR$_{11}$, —NR$_9$R$_{11}$, and —NR$_{11}$R$_{12}$;

R$_9$ is selected from the group consisting of aryl and heteroaryl, wherein said aryl and heteroaryl groups are optionally substituted with one or more groups independently selected from the group consisting of R$_{10}$ and R$_{11}$;

R$_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

R$_{11}$ and R$_{12}$ are independently selected from the group consisting of hydrogen, alkyl, haloalkyl, cycloalkyl, halocycloalkyl, alkenyl, haloalkenyl, alkynyl, and haloalkynyl;

R$_{13}$ and R$_{13a}$ are independently selected from the group consisting of a bond, —O—, —NR$_{11}$—, —NR$_{11}$C(=O)—, —NR$_{11}$C(=S)—, —NR$_{11}$C(=O)O—, —NR$_{11}$C(=O)NR$_{11}$—, —NR$_{11}$C(=S)NR$_{11}$—, —NR$_{11}$SO$_2$NR$_{11}$—, —NR$_{11}$SO$_2$—, —C(=NR$_7$)—, —C(=NR$_8$)—, —C(=O)—, —C(=O)—, —C(=O)NR$_{11}$—, —C(=S)NR$_{11}$—, —S(O)—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or (2) a salt thereof.

A third aspect of the invention is to provide (1) a dimeric 1-arylpyrazole compound of formula (III):

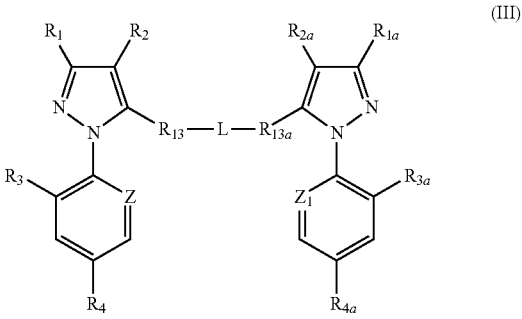

(III)

wherein:

R$_1$ and R$_{1a}$ are independently selected from the group consisting of hydrogen, cyano, halogen, R$_6$, —C(=O)R$_6$, —C(=O)R$_8$, —C(=O)NR$_{11}$R$_{12}$, —CH(=NR$_7$), —CH(=NR$_8$), —C(=NR$_7$)R$_7$, —C(=NR$_7$)R$_8$, —C(=NR$_8$)R$_7$, —C(=NNR$_7$)R$_7$, —C(=NNR$_7$)R$_8$, —C(=NNR$_8$)R$_7$, and —C(S)NR$_7$R$_{11}$;

R$_2$ and R$_{2a}$ are independently selected from the group consisting of S(O)$_n$R$_{11}$, and 4,5-dicyanoimidazol-2-yl;

R$_3$ and R$_{3a}$ are independently selected from the group consisting of hydrogen, halogen, cyano, nitro, alkyl, cycloalkyl, haloalkyl, alkoxy, and haloalkoxy;

$R_4$ and $R_{4a}$ are independently selected from the group consisting of halogen, cyano, nitro, $R_7$, $R_8$, —C(O)$R_{11}$, —C(=O)$NR_{11}R_{12}$, —C(=$NR_7$)$R_7$, —C(=$NR_7$)$R_8$, —C(=$NR_7$)$NR_{11}R_{12}$, —S(O)$_n R_{11}$, and $SF_5$;

Z and $Z_1$ are independently selected from the group consisting of a nitrogen atom and C—$R_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and $R_6$;

$R_8$ is selected from the group consisting of —$OR_9$, —$OR_{11}$, —$SR_9$, —$SR_{11}$, —$NR_9R_{11}$, and —$NR_{11}R_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —S(O)$_n R_{11}$, —S(O)$_n NR_{11}R_{12}$, —$NR_{11}R_{12}$, —$NR_{11}$(C=O)$R_{11}$, —$NR_{11}$(C=O)$NR_{11}R_{12}$, —$NR_{11}$S(O)$_n R_{11}$, —$NR_{11}$S(O)$_n NR_{11}R_{12}$, —C(=O)$R_{11}$, —C(=O)$OR_{11}$, —C(=O)$NR_{11}R_{12}$, —C(=S)$R_{11}$, —C(=S)$NR_{11}R_{12}$;

$R_{11}$ and $R_{12}$ are independently selected from the group consisting of hydrogen, alkyl, haloalkyl, cycloalkyl, halocycloalkyl, alkenyl, haloalkenyl, alkynyl, and haloalkynyl;

$R_{13}$ and $R_{13a}$ are independently selected from the group consisting of a bond, —O—, —$NR_{11}SO_2NR_{11}$—, —$NR_{11}SO_2$—, —C(=$NR_7$)—, —C(=$NR_8$)—, —C(=O)—, —C(=O)$NR_{11}$—, —C(=S)$NR_{11}$—, —C(=$NR_7$)$NR_{11}$, —S(O)$_n$—, and —S(O)$_n NR_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or (2) a salt thereof.

A fourth aspect of the present invention is to provide compositions for treatment of animals against ectoparasites, wherein the compositions comprise the compounds of the invention and an acceptable carrier.

A fifth aspect of the invention is to provide pesticidal methods of use of the dimeric 1-arylpyrazole compounds/compositions of the invention against ectoparasites (e.g. arthropods), in veterinary medicine or livestock husbandry, in public health, or in agricultural or horticultural crops.

A sixth aspect of the present invention is to provide compounds with high activity and improved safety to the user and the environment, which are obtained by optimization of chemical, physical and biological properties such as solubility, melting point, stability, electronic and steric parameters, and the like.

A seventh aspect of the present invention is to provide a method for preventing or interrupting the transmission of parasite-borne diseases from an actual or putative amplifying or incipient host, such as an animal or bird (wild or domesticated) or human, to a second actual or putative amplifying or incipient host, such as an animal, bird or human, using a composition comprising the dimeric 1-arylpyrazole compounds of the invention.

It is noted that the invention does not intend to encompass within the scope of the invention any previously disclosed compound, product, process of making the product or method of using the product, which meets the written description and enablement requirements of the USPTO (35 U.S.C. 112, first paragraph) or the EPO (Article 83 of the EPC), such that the applicant(s) reserve the right and hereby disclose a disclaimer of any previously described product, method of making the product or process of using the product. It is therefore an intention of the invention to not explicitly cover compounds, products, processes of making products or compounds, or methods of using products or compounds that are explicitly disclosed in the prior art or whose novelty is destroyed by prior art, including without limitation any prior art herein mentioned, including without limitation U.S. Pat. Nos. 5,122,530; 5,885,607; 6,010,710; 6,083,519; 6,096,329; 6,685,954; EP 0 234 119 and EP 0 295 117 (U.S. Pat. Nos. 5,232,940; 5,547,974; 5,608,077; 5,714,191; 5,916,618 and 6,372,774); EP 0 352 944 (U.S. Pat. No. 4,963,575); EP 0 780 378 (U.S. Pat. Nos. 5,817,688; 5,922,885; 5,994,386; 6,124,339; 6,180,798 and 6,395,906); EP 0 846 686 (U.S. Pat. No. 6,069,157); and the applicant(s) explicitly reserve the right to introduce into any claim a disclaimer as to any previously disclosed compound, product, process of making the product or method of using the product. Specifically, the compounds of the invention are not intended to encompass fipronil or previously disclosed derivatives of fipronil.

These and other embodiments are disclosed or are apparent from and encompassed by, the following Detailed Description.

DETAILED DESCRIPTION

As used herein, the following terms have the meanings ascribed to them unless specified otherwise. In this disclosure and in the claims, terms such as "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Unless otherwise specifically noted or apparent by context, "active agent" or "active ingredient" or "therapeutic agent" as used in this specification, means a dimeric 1-arylpyrazole compound of the invention It is also noted that in this disclosure and the appended claims and/or paragraphs, the term "dimeric 1-arylpyrazole" or "dimeric arylpyrazole" as used to describe the invention is intended to include all stereoisomers and crystalline forms (which include hydrated forms, polymorphic forms and amorphous forms with up to 15% by weight crystalline structure) thereof.

The term "animal" is used herein to include all mammals, birds and fish and also include all vertebrate animals, including humans. It also includes an individual animal in all stages of development, including embryonic and fetal stages.

For the purposes of this application, unless otherwise stated in the specification, the following terms have the definitions cited below:

(1) Alkyl refers to both straight and branched carbon chains. References to individual alkyl groups are specific for the straight chain (e.g. butyl=n-butyl). In one embodiment of alkyl, the number of carbon atoms is 1-20, in another embodiment of alkyl, the number of carbon atoms is 1-8 and in yet another embodiment of alkyl, the number of carbon atoms is 1-4. Other ranges of carbon numbers are also contemplated depending on the location of the alkyl moiety on the molecule.

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbon atoms is 2-20, in another embodiment of alkenyl, the number of carbon atoms is 2-8 and in yet another embodiment of alkenyl, the number of carbon atoms is 2-4. Other ranges of carbon-carbon double bonds and carbon numbers are also contemplated depending on the location of the alkenyl moiety on the molecule.

(3) Alkynyl refers to both straight and branched carbon chains which have at least one carbon-carbon triple bond. In one embodiment of alkynyl, the number of triple bonds is 1-3, in another embodiment of alkynyl, the number of triple bonds is one. In one embodiment of alkynyl, the number of carbon atoms is 2-20, in another embodiment of alkynyl, the number of carbon atoms is 2-8 and in yet another embodiment of alkynyl, the number of carbon atoms is 2-4. Other ranges of carbon-carbon triple bonds and carbon numbers are also contemplated depending on the location of the alkenyl moiety on the molecule.

(4) Aryl refers to a $C_6$-$C_{10}$ aromatic ring structure. In one embodiment of aryl, the moiety is phenyl, naphthyl, tetrahydronapthyl, phenylcyclopropyl and indanyl; in another embodiment of aryl, the moiety is phenyl.

(5) Alkoxy refers to —O-alkyl, wherein alkyl is as defined in (1).

(6) Thioalkyl refers to —S-alkyl, wherein alkyl is as defined in (1).

(7) Oxo refers to C=O.

(8) Oximino refers to C=N—OH.

(9) Alkoxyimino refers to C=N—O-alkyl, wherein alkyl is as defined in (1).

(10) Cyclo as a prefix (e.g. cycloalkyl, cycloalkenyl, cycloalkynyl) refers to a saturated or unsaturated cyclic ring structure having from three to eight carbon atoms in the ring, the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule.

(11) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—CH$_2$Cl), dichloromethyl (—CHCl$_2$), or trichloromethyl (—CCl$_3$)). The designation of "halo" (e.g. as illustrated in the term haloalkyl) also refers to substitution with one or more halogen atoms, which are independently selected (e.g. as illustrated with methyl as dichloromethyl (—CHCl$_2$), chlorofluoromethyl (—CHClF), or dichlorofluoromethyl (—CFCl$_2$)).

(12) Heterocycle, heterocyclic or heterocyclo refers to fully saturated or unsaturated, including aromatic (i.e. "heteroaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

It is a first object of the invention to provide a compound of formula (I):

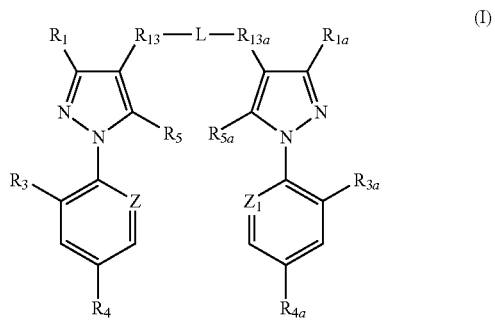

wherein:

$R_1$ and $R_{1a}$ are independently selected from the group consisting of hydrogen, cyano, halogen, $R_6$, —C(=O)$R_6$, —C(=O)$R_8$, —C(=O)NR$_{11}$R$_{12}$, —CH(=NR$_7$), —CH(=NR$_8$), —C(=NR$_7$)R$_7$, —C(=NR$_7$)R$_8$, —C(=NR$_8$)R$_7$, —C(=NNR$_7$)R$_7$, —C(=NNR$_7$)R$_8$, —C(=NNR$_8$)R$_7$, and —C(S)NR$_7$R$_{11}$;

$R_3$ and $R_{3a}$ are independently selected from the group consisting of hydrogen, halogen, cyano, nitro, alkyl, cycloalkyl, haloalkyl, alkoxy, and haloalkoxy;

$R_4$ and $R_{4a}$ are independently selected from the group consisting of halogen, cyano, nitro, $R_7$, $R_8$, —C(O)$R_{11}$, —C(=O)NR$_{11}$R$_{12}$, —C(=NR$_7$)R$_7$, —C(=NR$_7$)R$_8$, —C(=NR$_7$)NR$_{11}$R$_{12}$, —S(O)$_n$R$_{11}$, and SF$_5$;

$R_5$ and $R_{5a}$ are independently selected from the group consisting of $R_{10}$, $R_{11}$, —C(=NR$_7$)R$_7$, —C(=NR$_7$)R$_8$, —C(=NR$_8$)R$_7$, —C(=NR$_7$)NR$_{11}$R$_{12}$, —C(=S)NR$_{11}$R$_{12}$, —NR$_{11}$R$_{12}$, —NR$_{11}$C(=O)R$_8$, —NR$_{11}$C(=O)R$_{11}$, and —N=C(R$_{11}$)NR$_6$;

Z and $Z_1$ are independently selected from the group consisting of a nitrogen atom and C—R$_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and $R_6$;

$R_8$ is selected from the group consisting of —OR$_9$, —OR$_{11}$, —SR$_9$, —SR$_{11}$, —NR$_9$R$_{11}$, and —NR$_{11}$R$_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

$R_{11}$ and $R_{12}$ are independently selected from the group consisting of hydrogen, alkyl, haloalkyl, cycloalkyl, halocycloalkyl, alkenyl, haloalkenyl, alkynyl, and haloalkynyl;

$R_{13}$ and $R_{13a}$ are independently selected from the group consisting of a bond, —O—, —NR$_{11}$—, —NR$_{11}$C(=O)—, —NR$_{11}$C(=S)—, —NR$_{11}$C(=O)O—, —NR$_{11}$C(=O)NR$_{11}$—, —NR$_{11}$C(=S)NR$_{11}$—, —NR$_{11}$SO$_2$NR$_{11}$—, —NR$_{11}$SO$_2$—, —C(=NR$_7$)—, —C(=NR$_8$)—, —C(=O)—, —C(=O)NR$_{11}$—, —C(=S)NR$_{11}$—, —S(O)$_n$—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the first object of the invention provides for a compound of formula (I) wherein:

$R_1$ and $R_{1a}$ are independently selected from the group consisting of hydrogen, cyano, halogen, $R_6$, —C(=O)R$_6$, —C(=O)R$_8$, —C(=O)NR$_{11}$R$_{12}$, —CH(=NR$_7$), —CH(=NR$_8$), —C(=NR$_7$)R$_7$, —C(=NR$_7$)R$_8$, —C(=NR$_8$)R$_7$, and —C(S)NR$_7$R$_{11}$;

$R_3$ and $R_{3a}$ are independently selected from the group consisting of hydrogen, halogen, alkyl, cycloalkyl, haloalkyl, alkoxy, and haloalkoxy;

$R_4$ and $R_{4a}$ are independently selected from the group consisting of halogen, $R_7$, $R_8$, —S(O)$_n$R$_{11}$, and SF$_5$;

$R_5$ and $R_{5a}$ are independently selected from the group consisting of $R_{10}$, $R_{11}$, —C(=NR$_7$)R$_7$, —C(=NR$_7$)R$_8$, —C(=NR$_8$)R$_7$, —C(=NR$_7$)NR$_{11}$R$_{12}$, —C(=S)NR$_{11}$R$_{12}$, —NR$_{11}$R$_{12}$, and —N=C(R$_{11}$)NR$_6$;

Z and $Z_1$ are C—R$_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and $R_6$;

$R_8$ is selected from the group consisting of —OR$_9$, —OR$_{11}$, —SR$_9$, —SR$_{11}$, —NR$_9$R$_{11}$, and —NR$_{11}$R$_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —R$_{11}$R$_{12}$, —NR$_{11}$(C=O)R$_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

$R_{11}$ and $R_{12}$ are independently selected from the group consisting of hydrogen, alkyl, haloalkyl, cycloalkyl, halocycloalkyl, alkenyl, haloalkenyl, alkynyl, and haloalkynyl;

$R_{13}$ and $R_{13a}$ are independently selected from the group consisting of a —C(=NR$_7$)—, —C(=NR$_8$)—, —C(=O)—, —C(=O)NR$_{11}$—, —C(=S)NR$_{11}$—, —S(O)$_n$—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the first object of the invention provides for a compound of formula (I) wherein:

$R_1$ and $R_{1a}$ are independently selected from the group consisting of cyano, halogen, and —C(S)NR$_7$R$_{11}$;

$R_3$ and $R_{3a}$ are halogen;

$R_4$ and $R_{4a}$ are independently selected from the group consisting of halogen, haloalkyl, —S(O)—R$_{11}$, and SF$_5$;

$R_5$ and $R_{5a}$ are independently selected from the group consisting of alkyl, haloalkyl, —NR$_{11}$R$_{12}$, and —N=C(R$_{11}$)NR$_6$;

Z and $Z_1$ are C—R$_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and alkyl;

$R_8$ is selected from the group consisting of —OR$_9$, —OR$_{11}$, —SR$_9$, —SR$_{11}$, —NR$_9$R$_{11}$, and —NR$_{11}$R$_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

R$_{11}$ and R$_{12}$ are independently selected from the group consisting of hydrogen, alkyl, and haloalkyl;

R$_{13}$ and R$_{13a}$ are independently selected from the group consisting of a —C(=NR$_7$)—, —C(=NR$_8$)—, —C(=O)—, —C(=O)NR$_{11}$—, —C(=S)NR$_{11}$—, —S(O)$_n$—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the first object of the invention provides for a compound of formula (I) wherein:

R$_1$ and R$_{1a}$ are independently selected from the group consisting of cyano, and —C(S)NR$_7$R$_{11}$;

R$_3$ and R$_{3a}$ are halogen;

R$_4$ and R$_{4a}$ are haloalkyl;

R$_5$ and R$_{5a}$ are independently selected from the group consisting of alkyl, and —NR$_{11}$R$_{12}$;

Z and Z$_1$ are C—R$_3$;

R$_7$ is selected from the group consisting of H and alkyl;

R$_{11}$ and R$_{12}$ are hydrogen;

R$_{13}$ and R$_{13a}$ are —S(O)$_n$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the first object of the invention provides for a compound of formula (I) wherein:

R$_1$ and R$_{1a}$ are cyano;

R$_3$ and R$_{3a}$ are halogen;

R$_4$ and R$_{4a}$ are haloalkyl;

R$_5$ and R$_{5a}$ are independently selected from the group consisting of alkyl, and —NR$_{11}$R$_{12}$;

Z and Z$_1$ are C—R$_3$;

R$_{11}$ and R$_{12}$ are hydrogen;

R$_{13}$ and R$_{13a}$ are —S(O)$_n$—;

L is alkyl or haloalkyl; and n is 2; or a salt thereof.

It is a second object of the invention to provide a compound of formula (II):

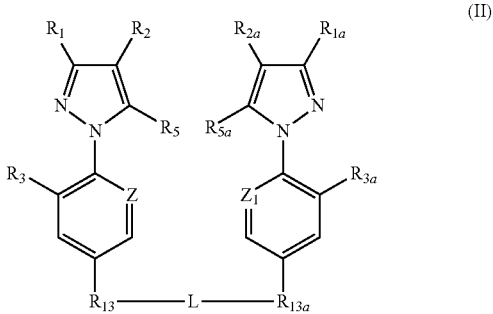

(II)

wherein:

R$_1$ and R$_{1a}$ are independently selected from the group consisting of hydrogen, cyano, halogen, R$_6$, —C(=O)R$_6$, —C(=O)R$_8$, —C(=O)NR$_{11}$R$_{12}$, —CH(=NR$_7$), —CH(=NR$_8$), —C(=NR$_7$)R$_7$, —C(=NR$_7$)R$_8$, —C(=NR$_8$)R$_7$, —C(=NNR$_7$)R$_7$, —C(=NNR$_7$)R$_8$, —C(=NNR$_8$)R$_7$, and —C(S)NR$_7$R$_{11}$;

R$_2$ and R$_{2a}$ are independently selected from the group consisting of S(O)$_n$R$_{11}$, and 4,5-dicyanoimidazol-2-yl;

R$_3$ and R$_{3a}$ are independently selected from the group consisting of hydrogen, halogen, cyano, nitro, alkyl, cycloalkyl, haloalkyl, alkoxy, and haloalkoxy;

R$_5$ and R$_{5a}$ are independently selected from the group consisting of R$_{10}$, R$_{11}$, —C(=NR$_7$)R$_7$, —C(=NR$_7$)R$_8$, —C(=NR$_8$)R$_7$, —C(=NR$_7$)NR$_{11}$R$_{12}$, —C(=S)NR$_{11}$R$_{12}$, —NR$_{11}$R$_{12}$, —NR$_{11}$C(=O)R$_8$, —NR$_{11}$C(=O)R$_{11}$, and —N=C(R$_{11}$)NR$_6$;

Z and Z$_1$ are independently selected from the group consisting of a nitrogen atom and C—R$_3$;

R$_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of R$_8$, R$_9$ and R$_{10}$;

R$_7$ is selected from the group consisting of H and R$_6$;

R$_8$ is selected from the group consisting of —OR$_9$, —OR$_{11}$, —SR$_9$, —SR$_{11}$, —NR$_9$R$_{11}$, and —NR$_{11}$R$_{12}$;

R$_9$ is selected from the group consisting of aryl and heteroaryl, wherein said aryl and heteroaryl groups are optionally substituted with one or more groups independently selected from the group consisting of R$_{10}$ and R$_{11}$;

R$_{10}$ is selected from the group consisting of cyano, nitro, hydroxyl, halogen, alkyl, cycloalkyl, haloalkyl, alkoxy, haloalkoxy, —S(O)—R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

R$_{11}$ and R$_{12}$ are independently selected from the group consisting of hydrogen, alkyl, haloalkyl, cycloalkyl, halocycloalkyl, alkenyl, haloalkenyl, alkynyl, and haloalkynyl;

R$_{13}$ and R$_{13a}$ are independently selected from the group consisting of a bond, —O—, —NR$_{11}$—, —NR$_{11}$C(=O)—, —NR$_{11}$C(=S)—, —NR$_{11}$C(=O)O—, —NR$_{11}$C(=O)NR$_{11}$—, —NR$_{11}$C(=S)NR$_{11}$—, —NR$_{11}$SO$_2$NR$_{11}$—, —$NR_{11}SO_2$—, —$C(=NR_7)$—, —$C(=NR_8)$—, —$C(=O)$—, —$C(=O)NR_{11}$—, —$C(=S)NR_{11}$—, —$S(O)_n$—, and —$S(O)_nNR_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the second object of the invention provides for a compound of formula (II) wherein:

$R_1$ and $R_{1a}$ are independently selected from the group consisting of hydrogen, cyano, halogen, $R_6$, —$C(=O)R_6$, —$C(=O)R_8$, —$C(=O)NR_{11}R_{12}$, —$CH(=NR_7)$, —$CH(=NR_8)$, —$C(=NR_7)R_7$, —$C(=NR_7)R_8$, —$C(=NR_8)R_7$, and —$C(S)NR_7R_{11}$;

$R_2$ and $R_{2a}$ are independently selected from the group consisting of $S(O)_nR_{11}$, and 4,5-dicyanoimidazol-2-yl;

$R_3$ and $R_{3a}$ are independently selected from the group consisting of hydrogen, halogen, alkyl, cycloalkyl, haloalkyl, alkoxy, and haloalkoxy;

$R_5$ and $R_{5a}$ are independently selected from the group consisting of $R_{10}$, $R_{11}$, —$C(=NR_7)R_7$, —$C(=NR_7)R_8$, —$C(=NR_8)R_7$, —$C(=NR_7)NR_{11}R_{12}$, —$C(=S)NR_{11}R_{12}$, —$NR_{11}R_{12}$, and —$N=C(R_{11})NR_6$;

Z and $Z_1$ are C—$R_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and $R_6$;

$R_8$ is selected from the group consisting of —$OR_9$, —$OR_{11}$, —$SR_9$, —$SR_{11}$, —$NR_9R_{11}$, and —$NR_{11}R_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —$S(O)$—$R_{11}$, —$S(O)_nNR_{11}R_{12}$, —$NR_{11}R_{12}$, —$NR_{11}(C=O)R_{11}$, —$NR_{11}(C=O)NR_{11}R_{12}$, —$NR_{11}S(O)_nR_{11}$, —$NR_{11}S(O)_nNR_{11}R_{12}$, —$C(=O)R_{11}$, —$C(=O)OR_{11}$, —$C(=O)NR_{11}R_{12}$, —$C(=S)R_{11}$, —$C(=S)NR_{11}R_{12}$;

$R_{11}$ and $R_{12}$ are independently selected from the group consisting of hydrogen, alkyl, haloalkyl, cycloalkyl, halocycloalkyl, alkenyl, haloalkenyl, alkynyl, and haloalkynyl;

$R_{13}$ and $R_{13a}$ are independently selected from the group consisting of a bond, —O—, —$S(O)_n$—, and —$S(O)_nNR_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the second object of the invention provides for a compound of formula (II) wherein:

$R_1$ and $R_{1a}$ are independently selected from the group consisting of cyano, halogen, and —$C(S)NR_7R_{11}$;

$R_2$ and $R_{2a}$ are independently selected from the group consisting of $S(O)_nR_{11}$, and 4,5-dicyanoimidazol-2-yl;

$R_3$ and $R_{3a}$ are halogen;

$R_5$ and $R_{5a}$ are independently selected from the group consisting of alkyl, haloalkyl, —$NR_{11}R_{12}$, and —$N=C(R_{11})NR_6$;

Z and $Z_1$ are C—$R_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and alkyl;

$R_8$ is selected from the group consisting of —$OR_9$, —$OR_{11}$, —$SR_9$, —$SR_{11}$, —$NR_9R_{11}$, and —$NR_{11}R_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —$S(O)$—$R_{11}$, —$S(O)_nNR_{11}R_{12}$, —$NR_{11}R_{12}$, —$NR_{11}(C=O)R_{11}$, —$NR_{11}(C=O)NR_{11}R_{12}$, —$NR_{11}S(O)_nR_{11}$, —$NR_{11}S(O)_nNR_{11}R_{12}$, —$C(=O)R_{11}$, —$C(=O)OR_{11}$, —$C(=O)NR_{11}R_{12}$, —$C(=S)R_{11}$, —$C(=S)NR_{11}R_{12}$;

$R_{11}$ and $R_{12}$ are independently selected from the group consisting of hydrogen, alkyl, and haloalkyl;

$R_{13}$ and $R_{13a}$ are independently selected from the group consisting of a bond, —O—, —$S(O)_n$—, and —$S(O)_nNR_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the second object of the invention provides for a compound of formula (II) wherein:

$R_1$ and $R_{1a}$ are independently selected from the group consisting of cyano, and —$C(S)NR_7R_{11}$;

$R_2$ and $R_{2a}$ are independently selected from the group consisting of $S(O)_nR_{11}$, and 4,5-dicyanoimidazol-2-yl;

$R_3$ and $R_{3a}$ are halogen;

$R_5$ and $R_{5a}$ are independently selected from the group consisting of alkyl, and —$NR_{11}R_{12}$;

Z and $Z_1$ are C—$R_3$;

$R_7$ is selected from the group consisting of H and alkyl;

$R_{11}$ and $R_{12}$ are independently selected from the group consisting of hydrogen, alkyl, and haloalkyl;

$R_{13}$ and $R_{13a}$ are independently selected from the group consisting of a bond and —$S(O)_n$—; L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the second object of the invention provides for a compound of formula (II) wherein:

$R_1$ and $R_{1a}$ are cyano;

$R_2$ and $R_{2a}$ are independently selected from the group consisting of $S(O)_nR_{11}$, and 4,5-dicyanoimidazol-2-yl;

$R_3$ and $R_{3a}$ are halogen;

$R_4$ and $R_{4a}$ are haloalkyl;

$R_5$ and $R_{5a}$ are independently selected from the group consisting of alkyl, and —$NR_{11}R_{12}$;

Z and $Z_1$ are C—$R_3$;

$R_{11}$ and $R_{12}$ are independently selected from the group consisting of hydrogen, alkyl, and haloalkyl;

$R_{13}$ and $R_{13a}$ are a bond;

L is alkyl or haloalkyl; and n is 2; or a salt thereof.

It is a third object of the invention to provide a compound of formula (III):

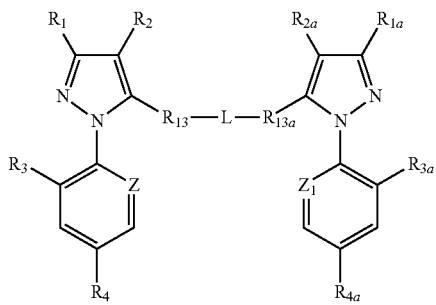

(III)

wherein:

$R_1$ and $R_{1a}$ are independently selected from the group consisting of hydrogen, cyano, halogen, $R_6$, —C(=O)$R_6$, —C(=O)$R_8$, —C(=O)$NR_{11}R_{12}$, —CH(=$NR_7$), —CH(=$NR_8$), —C(=$NR_7$)$R_7$, —C(=$NR_7$)$R_8$, —C(=$NR_8$)$R_7$, —C(=$NNR_7$)$R_7$, —C(=$NNR_7$)$R_8$, —C(=$NNR_8$)$R_7$, and —C(S)$NR_7R_{11}$;

$R_2$ and $R_{2a}$ are independently selected from the group consisting of S(O)—$R_{11}$, and 4,5-dicyanoimidazol-2-yl;

$R_3$ and $R_{3a}$ are independently selected from the group consisting of hydrogen, halogen, cyano, nitro, alkyl, cycloalkyl, haloalkyl, alkoxy, and haloalkoxy;

$R_4$ and $R_{4a}$ are independently selected from the group consisting of halogen, cyano, nitro, $R_7$, $R_8$, —C(O)$R_{11}$, —C(=O)$NR_{11}R_{12}$, —C(=$NR_7$)$R_7$, —C(=$NR_7$)$R_8$, —C(=$NR_7$)$NR_{11}R_{12}$, —S(O)—$R_{11}$, and $SF_5$;

Z and $Z_1$ are independently selected from the group consisting of a nitrogen atom and C—$R_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and $R_6$;

$R_8$ is selected from the group consisting of —$OR_9$, —$OR_{11}$, —$SR_9$, —$SR_{11}$, —$NR_9R_{11}$, and —$NR_{11}R_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —S(O)—$R_{11}$, —$S(O)_nNR_{11}R_{12}$, —$NR_{11}R_{12}$, —$NR_{11}$(C=O)$R_{11}$, —$NR_{11}$(C=O)$NR_{11}R_{12}$, —$NR_{11}$S(O)—$R_{11}$, —$NR_{11}$S(O)—$NR_{11}R_{12}$, —C(=O)$R_{11}$, —C(=O)$OR_{11}$, —C(=O)$NR_{11}R_{12}$, —C(=S)$R_{11}$, —C(=S)$NR_{11}R_{12}$;

$R_{11}$ and $R_{12}$ are independently selected from the group consisting of hydrogen, alkyl, haloalkyl, cycloalkyl, halocycloalkyl, alkenyl, haloalkenyl, alkynyl, and haloalkynyl;

$R_{13}$ and $R_{13a}$ are independently selected from the group consisting of a bond, —O—, —$NR_{11}SO_2NR_{11}$—, —$NR_{11}SO_2$—, —C(=$NR_7$)—, —C(=$NR_8$)—, —C(=O)—, —C(=O)$NR_{11}$—, —C(=S)$NR_{11}$—, —C(=$NR_7$)$NR_{11}$, —S(O)—, and —$S(O)_nNR_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the third object of the invention provides for a compound of formula (III) wherein:

$R_1$ and $R_{1a}$ are independently selected from the group consisting of hydrogen, cyano, halogen, $R_6$, —C(=O)$R_6$, —C(=O)$R_8$, —C(=O)$NR_{11}R_{12}$, —CH(=$NR_7$), —CH(=$NR_8$), —C(=$NR_7$)$R_7$, —C(=$NR_7$)$R_8$, —C(=$NR_8$)$R_7$, and —C(S)$NR_7R_{11}$;

$R_2$ and $R_{2a}$ are independently selected from the group consisting of $S(O)_nR_{11}$, and 4,5-dicyanoimidazol-2-yl;

$R_3$ and $R_{3a}$ are independently selected from the group consisting of hydrogen, halogen, alkyl, cycloalkyl, haloalkyl, alkoxy, and haloalkoxy;

$R_4$ and $R_{4a}$ are independently selected from the group consisting of halogen, $R_7$, $R_8$, —$S(O)_nR_{11}$, and $SF_5$;

Z and $Z_1$ are C—$R_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and $R_6$;

$R_8$ is selected from the group consisting of —$OR_9$, —$OR_{11}$, —$SR_9$, —$SR_{11}$, —$NR_9R_{11}$, and —$NR_{11}R_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)—R$_{11}$, —NR$_{11}$S(O)—NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

R$_{11}$ and R$_{12}$ are independently selected from the group consisting of hydrogen, alkyl, haloalkyl, cycloalkyl, halocycloalkyl, alkenyl, haloalkenyl, alkynyl, and haloalkynyl;

R$_{13}$ and R$_{13a}$ are independently selected from the group consisting of a bond, —O—, —NR$_{11}$SO$_2$NR$_{11}$—, —NR$_{11}$SO$_2$—, —C(=NR$_7$)—, —C(=NR$_8$)—, —C(=O)—, —C(=O)NR$_{11}$—, —C(=S)NR$_{11}$—, —C(=NR$_7$)NR$_{11}$, —S(O)—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the third object of the invention provides for a compound of formula (III) wherein:

R$_1$ and R$_{1a}$ are independently selected from the group consisting of cyano, halogen, and —C(S)NR$_7$R$_{11}$;

R$_2$ and R$_{2a}$ are independently selected from the group consisting of S(O)$_n$R$_{11}$, and 4,5-dicyanoimidazol-2-yl;

R$_3$ and R$_{3a}$ are halogen;

R$_4$ and R$_{4a}$ are independently selected from the group consisting of halogen, haloalkyl, —S(O)$_n$R$_{11}$, and SF$_5$;

Z and Z$_1$ are C—R$_3$;

R$_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of R$_8$, R$_9$ and R$_{10}$;

R$_7$ is selected from the group consisting of H and alkyl;

R$_8$ is selected from the group consisting of —OR$_9$, —OR$_{11}$, —SR$_9$, —SR$_{11}$, —NR$_9$R$_{11}$, and —NR$_{11}$R$_{12}$;

R$_9$ is selected from the group consisting of aryl and heteroaryl, wherein said aryl and heteroaryl groups are optionally substituted with one or more groups independently selected from the group consisting of R$_{10}$ and R$_{11}$;

R$_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

R$_{11}$ and R$_{12}$ are independently selected from the group consisting of hydrogen, alkyl, and haloalkyl;

R$_{13}$ and R$_{13a}$ are independently selected from the group consisting of a bond, —NR$_{11}$SO$_2$NR$_{11}$—, —NR$_{11}$SO$_2$—, —C(=NR$_7$)—, —C(=NR$_8$)—, —C(=O)NR$_{11}$—, —C(=S)NR$_{11}$—, —S(O)$_n$—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the third object of the invention provides for a compound of formula (III) wherein:

R$_1$ and R$_{1a}$ are independently selected from the group consisting of cyano, and —C(S)NR$_7$R$_{11}$;

R$_2$ and R$_{2a}$ are independently selected from the group consisting of S(O)$_n$R$_{11}$, and 4,5-dicyanoimidazol-2-yl;

R$_3$ and R$_{3a}$ are halogen;

R$_4$ and R$_{4a}$ are haloalkyl;

Z and Z$_1$ are C—R$_3$;

R$_7$ is selected from the group consisting of H and alkyl;

R$_{11}$ and R$_{12}$ are independently selected from the group consisting of hydrogen, alkyl, and haloalkyl;

R$_{13}$ and R$_{13a}$ a bond;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

Another embodiment of the third object of the invention provides for a compound of formula (III) wherein:

R$_1$ and R$_{1a}$ are cyano;

R$_2$ and R$_{2a}$ are independently selected from the group consisting of S(O)$_n$R$_{11}$, and 4,5-dicyanoimidazol-2-yl;

R$_3$ and R$_{3a}$ are halogen;

R$_4$ and R$_{4a}$ are haloalkyl;

Z and Z$_1$ are C—R$_3$;

R$_{11}$ is haloalkyl;

R$_{13}$ and R$_{13a}$ are a bond;

L is alkyl or haloalkyl; and n is 2; or a salt thereof.

It is a further object of the invention to provide for a composition for treatment of animals against ectoparasites and/or endoparasites comprising the compound of any one of formulas (I)-(III) and an acceptable carrier.

It is still a further object of the invention to provide for the use of the composition comprising the compound of any one of formulas (I)-(III) in the manufacture of a medicament for the therapeutic and/or prophylactic treatment of an animal against an ectoparasite and/or an endoparasite.

It is still a further object of the invention to provide for an insecticidal composition comprising the compound of any one of formulas (I)-(III) and an acceptable carrier.

It is still a further object of the invention to provide for the use of a compound of any one of formulas (I)-(III) in the manufacture of a composition for controlling pests.

It is still a further object of the invention to provide for a method for the preparation of pesticidal compositions, characterized in that a compound of any one of formulas (I)-(III) is mixed with extenders and/or surface-active substances.

It is still a further object of the invention to provide for a method for controlling pests, wherein a compound of any one of formulas (I)-(III) or a composition comprising the compound of any one of formulas (I)-(III) is allowed to act on the pests and/or their environment or on the plants, plant parts, seeds, soils, areas, materials or spaces to be kept free from them.

It is still a further object of the invention to provide for the use of a compound of any one of formulas (I)-(III) or a composition comprising the compound of any one of formulas (I)-(III) for controlling pests.

It is still a further object of the invention to provide for the use of a compound of any one of formulas (I)-(III) or a composition comprising the compound of any one of formulas (I)-(III) for treating transgenic plants.

Also contemplated within the scope of the invention are acid or base salts, where applicable, of the dimeric aryl pyrazoles provided for herein.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

Ectoparasiticidal compositions of the invention comprise a dimeric aryl pyrazole and an acceptable carrier, for example a veterinarily acceptable carrier or an ectoparasiticidally acceptable carrier. In one embodiment of the invention, the ectoparasiticidally acceptable carrier is an organic solvent commonly used in the formulation art. These organic solvents may be found, for example, in Remington Pharmaceutical Science, 16$^{th}$ Edition (1986). These solvents include, for example, acetone, ethyl acetate, methanol, ethanol, isopropanol, dimethylformamide, dichloromethane or diethylene glycol monoethyl ether (Transcutol). These solvents can be supplemented by various excipients according to the nature of the desired phases, such as $C_8$-$C_{10}$ caprylic/capric triglyceride (Estasan or Miglyol 812), oleic acid or propylene glycol.

The composition of the invention can be in a variety of forms which include, but are not limited to, oral formulations, injectable formulations, and topical, dermal or subdermal formulations.

The composition of the invention may be in a form suitable for oral use, for example, as baits (see, e.g., U.S. Pat. No. 4,564,631), dietary supplements, troches, lozenges, chewables, tablets, hard or soft capsules, emulsions, aqueous or oily suspensions, aqueous or oily solutions, oral drench formulations, dispersible powders or granules, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides. In another embodiment of the oily phase, the triglycerides are medium-chain triglycerides, for example $C_8$-$C_{10}$ caprylic/capric triglyceride. Another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, the ratiow will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889. In addition to the active agent of the invention, the paste can also contain fumed silica; a viscosity modifier; a carrier; optionally, an absorbent; and optionally, a colorant, stabilizer, surfactant, or preservative.

The process for preparing a paste formulation comprises the steps of:
(a) dissolving or dispersing the active agent into the carrier by mixing;
(b) adding the fumed silica to the carrier containing the dissolved active agent compound and mixing until the silica is dispersed in the carrier;
(c) allowing the intermediate formed in (b) to settle for a time sufficient in order to allow the air entrapped during step (b) to escape; and
(d) adding the viscosity modifier to the intermediate with mixing to produce a uniform paste.

The above steps are illustrative, but not limiting. For example, step (a) can be the last step.

In one embodiment of the formulation, the formulation is a paste containing the active agent compound, fumed silica, a viscosity modifier, an absorbent, a colorant; and a hydrophilic carrier which is a triacetin, a monoglyceride, a diglyceride, or a triglyceride.

The paste may also include, but is not limited to, a viscosity modifier selected from the group consisting of PEG 200, PEG 300, PEG 400, PEG 600, monoethanolamine, triethanolamine, glycerol, propylene glycol, polyoxyethylene (20) sorbitan mono-oleate (polysorbate 80 or Tween 80), and polyoxamers (e.g., Pluronic L 81); an absorbent selected from the group consisting of magnesium carbonate, calcium carbonate, starch, and cellulose and its derivatives; and a colorant selected from the group consisting of titanium dioxide iron oxide, and FD&C Blue #1 Aluminum Lake.

The compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, ready-to-use formulations, spot-on solutions and suspensions. Topical application of an inventive compound or of a composition including at least one inventive compound among active agent(s) therein, a spot-on composition, can allow for the inventive compound to be distributed through the glands (e.g. sebaceous glands) of the animal and/or allow active agent(s) to achieve a systemic effect (plasma concentration) or throughout the haircoat. When the compound is distributed throughout glands, the glands can act as a reservoir, whereby there can be a long-lasting, e.g. 1-2 months effect. Spot-on formulations are typically applied in a localized region which refers to an area other than the entire animal. In one embodiment of a localized region, the location is between the shoulders. In another embodiment, the localized region is a stripe, e.g. a stripe from head to tail of the animal.

Pour-on formulations are described, for example, in U.S. Pat. No. 6,010,710. The pour-on formulations are advantageously oily, and generally comprise a diluent or vehicle and also a solvent (e.g. an organic solvent) for the active ingredient if the latter is not soluble in the diluent.

Organic solvents that can be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, mention may be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent will be added. One embodiment of the emollient and/or spreading and/or film-forming agents are those agents selected from the group consisting of:
(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil,
(b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil),
(c) cationic surfactants such as water-soluble quaternary ammonium salts of formula N'R'R"R'"R""Y$^-$, in which the R radicals are optionally hydroxylated hydrocarbon radicals and Y$^-$ is an anion of a strong acid such as the halide, sulphate and sulphonate anions; cetyltrimethylammonium bromide is among the cationic surfactants which can be used,
(d) amine salts of formula N$^+$ R'R"R'" in which the R radicals are optionally hydroxylated hydrocarbon radicals; octadecylamine hydrochloride is among the cationic surfactants which can be used,
(e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide,
(f) amphoteric surfactants such as the substituted lauryl compounds of betaine, and
(g) a mixture of at least two of these agents.

The solvent will be used in proportion with the concentration of the active agent compound and its solubility in this solvent. It will be sought to have the lowest possible volume. The vehicle makes up the difference to 100%.

In one embodiment of the amount of emollient, the emollient is used in a proportion selected from the group consisting of from about 0.1 to about 10%, and about 0.25 to about 5%, by volume.

In another embodiment of the invention, the composition can be in ready-to-use solution form as is described, for example, in U.S. Pat. No. 6,395,765. In addition to the active agent compound, the ready-to-use solution can contain a crystallization inhibitor, an organic solvent and an organic co-solvent.

The crystallization inhibitor can be present in a proportion selected from the group consisting of about 1 to about 20% (w/v) and about 5 to about 15% (w/v). Acceptable inhibitors are those whose addition provides for few (e.g. less than ten crystals) or no crystal. The organic solvent has a dielectric constant of a range selected from the group consisting of between about 10 and about 35, and between about 20 and about 30, the content of this organic solvent in the overall composition representing the complement to 100% of the composition. The organic co-solvent has a boiling point selected from the ranges consisting of below 100° C., and below 80° C., and a dielectric constant of a range selected from the group consisting of between about 10 and about 40, and between about 20 and about 30. This co-solvent may be present in the composition in an organic co-solvent/organic solvent weight/weight (W/W) ratio of between about 1/15 and about 1/2. The co-solvent is volatile so as to act as a drying promoter, and is miscible with water and/or with the organic solvent.

Crystallization inhibitors which are useful for the invention include but are not limited to:
(a) polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others;
(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);
(c) cationic surfactants, such as water-soluble quaternary ammonium salts of formula N$^+$R'R"R'"R""Y$^-$, in which the R radicals are identical or different optionally hydroxylated hydrocarbon radicals and Y$^-$ is an anion of a strong acid, such as halide, sulphate and sulphonate anions; cetyltrimethylammonium bromide is one of the cationic surfactants which can be used;
(d) amine salts of formula N$^+$R'R"R'", in which the R radicals are identical or different optionally hydroxylated hydrocarbon radicals; octadecylamine hydrochloride is one of the cationic surfactants which can be used;
(e) non-ionic surfactants, such as optionally polyoxyethylenated esters of sorbitan, e.g.

Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents can be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants. In another embodiment of the surface active agents, the agent is a polyoxyethylenated esters of sorbitan. In yet another embodiment of the surface-active agent, the agents include the various grades of polysorbate, for example Polysorbate 80.

In another embodiment of the invention, the film-forming agent and the surface-active agent can be incorporated in similar or identical amounts within the limit of the total amounts of crystallization inhibitor mentioned above.

The pair thus constituted secures, in a noteworthy way, the objectives of absence of crystallization on the coat and of maintenance of the cosmetic appearance of the skin or fur, that is to say without a tendency towards sticking or towards a sticky appearance, despite the high concentration of active material.

The formulation can also comprise an antioxidizing agent intended to inhibit oxidation in air, this agent being present in a proportion selected from a range consisting of about 0.005 to about 1% (w/v), and about 0.01 to about 0.05% (w/v).

In one embodiment of the antioxidizing agents, the agents are those conventional in the art and include, but are not limited to, butylated hydroxyanisole, butylated hydroxytoluene, ascorbic acid, sodium metabisulphite, propyl gallate, sodium thiosulphate or a mixture of not more than two of them.

The formulation adjuvants are well known to the practitioner in this art and may be obtained commercially or through known techniques. These concentrated compositions are generally prepared by simple mixing of the constituents as defined above. Advantageously, the starting point is to mix the active material in the main solvent and then the other ingredients or adjuvants are added.

The volume applied can be of the order of about 0.3 to about 1 ml. In one embodiment of the volume, the volume is on the order of about 0.5 ml for cats, and on the order of about 0.3 to about 3 ml for dogs, depending on the weight of the animal.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described, for example, in U.S. Pat. No. 6,426,333, where one embodiment of the spot-on formulation comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol.

The liquid carrier vehicle can optionally contain a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters, lecithin, sodium carboxymethylcellulose, and acrylic derivatives, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

In one embodiment of the invention, the active agent is present in the formulation at a concentration of about 0.05 to 10% weight/volume. In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

The composition containing the active agent of the invention may be administered continuously, for treatment or prophylaxis, by known methods. Generally, a dose of from about 0.001 to about 100 mg per kg of body weight of the active agent given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In another embodiment, the treatment is via a direct topical administration such as a paste, pour-on, ready-to-use, spot-on, etc. type formulation. Higher amounts may be provided for very prolonged release in or on the body of the animal. In another embodiment, the amount of the active ingredient for birds and animals which are small in size is greater than about 0.01 mg/kg, and in another embodiment for the treatment of small sized birds and animals, the amount of the active agent is between about 1 and about 100 mg/kg of weight of animal.

In one embodiment, a direct pour-on skin formulation according to the present invention can provide long-lasting and broad-spectrum efficacy when the solution is applied to the animal's back, e.g. along the line of the back at one or more points. According to a first embodiment for administering direct pour-on formulations, the process comprises applying the solution to the animals, the application being repeated every month or every two months. According to a second embodiment for administering direct pour-on formulation, the process comprises applying the solution to livestock animals before they arrive in the Feed Lot, it being possible for this application to be the final one before the animals are slaughtered. Obviously, the process may also consist in combining these two embodiments, namely the first followed by the second.

The solutions according to the invention may be applied using any means known per se, e.g. using an applicator gun or a metering flask.

The method serves to cleanse the skin and the hairs of the animals by eliminating the parasites which are present thereon, as well as their residues and dejections. The result of this is that the animals are no longer stressed by the parasites and their bites, this having positive consequences, for example on their growth and on the use of their food ration.

In another embodiment, the compounds of the invention are administered in spot-on formulations. The application of spot-on formulations according to the present invention can also obtain long-lasting and broad-spectrum efficacy when the solution is applied to the mammal or bird. Administration of the spot-on formulation may be intermittent in time and may be administered daily, weekly, biweekly, monthly, bimonthly, quarterly, or even for longer durations of time. The time period between treatments depends upon factors such as the parasite(s) being treated, the degree of infestation, the type of mammal or bird and the environment where it resides. It is well within the skill level of the practitioner to determine a specific administration period for a particular situation. This invention contemplates a method for permanently combating a parasite in an environment in which the animal is subjected to strong parasitic pressure where the administration is at a frequency far below a daily administration in this case. For example, it is preferable for the treatment according to the invention to be carried out monthly on dogs and on cats.

While not wishing to be bound by theory, it is believed that these formulations work by dissolution of the dose in the natural oils of the host's skin, fur or feathers. From there, the active agent(s) distribute around the host's body through the sebaceous glands of the skin. The therapeutic agent also remains in the sebaceous glands. Thus, the glands provide a natural reservoir for the active agent that allows for the agent to be drained back out to the follicles to reapply itself to the skin and hair. This, in turn, provides for longer time periods between applications as well as eliminating the need to re-administer the dose after the host becomes wet because of rain, bathes, etc. The inventive formulation has the further advantage of not being directly deposited on the skin or fur, where self-grooming animals could orally ingest the therapeutic agent, thereby becoming sick or possibly interacting with other therapeutic agent being orally administered.

The administration of spot-on formulations also provides for a method for cleaning the coats and the skin of animals by removal of the parasites which are present and of their waste and excreta. The animals treated thus exhibit a coat which is more pleasing to the eye and more pleasant to the touch.

In one embodiment of the location of administration, a single formulation containing the active agent in a substantially liquid carrier and in a form which makes possible a single application, or an application repeated a small number of times, will be administered to the animal over a localized region of the animal, e.g. between the two shoulders. In one embodiment of the invention, the localized region has a surface area of about 10 cm$^2$ or larger. In another embodiment of the invention, the localized region has a surface area of between about 5 and about 10 cm$^2$.

Other routes of administration include paste formulation, oral drench formulation, chewable formulation, transdermal or transmucosal patch or liquid, gel or paste, solution for inhalation and injectable formulation.

Additional active ingredients may be included in the compositions of the invention. These addition active agents include, but are not limited to, acaricides, anthelmintics, antiparasitics (both endoparasiticidal and ectoparasiticidal agents) and insecticides, may also be added to the compositions of the invention. Agents that are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) which may be used in the compositions include, but are not limited to, acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil HCl, allopurinol, alprazolam, altrenogest, amantadine HCl, amikacin sulfate, aminocaproic acid, aminopentamide hydrogen sulfate, aminophylline/theophylline, amiodarone HCl, amitraz, amitriptyline HCl, amlodipine besylate, ammonium chloride, ammonium molybdenate, amoxicillin, amoxicillin, clavulanate potassium, amphotericin B desoxycholate, amphotericin B lipid-based, ampicillin, amprolium HCl, antacids (oral), antivenin, apomorphione HCl, apramycin sulfate, ascorbic acid, asparaginase, aspiring, atenolol, atipamezole HCl, atracurium besylate, atropine sulfate, aurnofin, aurothioglucose, azaperone, azathioprine, azithromycin, baclofen, barbituates, benazepril HCl, betamethasone, bethanechol chloride, bisacodyl, bismuth subsalicylate, bleomycin sulfate, boldenone undecylenate, bromides, bromocriptine mesylate, budenoside, buprenorphine HCl, buspirone HCl, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur HCl, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine HCl, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol HCl, clindamycin, clofazimine, clomipramine HCl, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine HCl, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine HCl, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin HCl, digoxin, dihydrotachysterol (DHT), diltiazem HCl, dimenhydrinate, dimercaprol/BAL, dimethyl sulfoxide, dinoprost tromethamine, diphenylhydramine HCl, disopyramide phosphate, dobutamine HCl, docusate/DSS, dolasetron mesylate, domperidone, dopamine HCl, doramectin, doxapram HCl, doxepin HCl, doxorubicin HCl, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol HCl, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine HCL, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (Oxyglobin®), heparin, hetastarch, hyaluronate sodium, hydrazaline HCl, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol HCl, isotretinoin, isoxsuprine HCl, itraconazole, ivermectin, kaolin/pectin, ketamine HCl, ketoconazole, ketoprofen, ketorolac tromethamine, lactulose, leuprolide, levamisole, levetiracetam, levothyroxine sodium, lidocaine HCl, lincomycin HCl, liothyronine sodium, lisinopril, lomustine (CCNU), lufenuron, lysine, magnesium, mannitol, marbofloxacin, mechlorethamine HCl, meclizine HCl, meclofenamic acid, medetomidine HCl, medium chain triglycerides, medroxyprogesterone acetate, megestrol acetate, melarsomine, melatonin, meloxican, melphalan, meperidine HCl, mercaptopurine, meropenem, metformin HCl, methadone HCl, methazolamide, methenamine mandelate/hippurate, methimazole, methionine, methocarbamol, methohexital sodium, methotrexate, methoxyflurane, methylene blue, methylphenidate, methylprednisolone, metoclopramide HCl, metoprolol, metronidaxole, mexiletine HCl, mibolerone, midazolam HCl milbemycin oxime, mineral oil, minocycline HCl, misoprostol, mitotane, mitoxantrone HCl, morantel tartrate, morphine sulfate, moxidectin, naloxone HCl, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone HCl, oxytretracycline, oxytocin, pamidronate disodium, pancreplipase, pancuronium bromide, paromomycin sulfate, parozetine HCl, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine HCl, pheylbutazone, phenylephrine HCL, phenypropanolamine HCl, phenytoin sodium, pheromones, parenteral phosphate, phytonadione/vitamin K-1, pimobendan, piperazine, pirlimycin HCL, piroxicam, polysulfated glycosaminoglycan, ponazuril, potassium chloride, pralidoxime chloride, praziquantel, prazosin HCl, prednisolone/prednisone, primidone, procainamide HCl, procarbazine HCl, prochlorperazine, propantheline bromide, propionibacterium acnes injection, propofol, propranolol HCl, protamine sulfate, pseudoephedrine HCl, psyllium hydrophilic mucilloid, pyrantel pamoate, pyridostigmine bromide, pyrilamine maleate, pyrimethamine, quinacrine HCl, quinidine, ranitidine HCl, rifampin, s-adenosyl-methionine (SAMe), saline/hyperosmotic laxative, selamectin, selegiline HCL/l-deprenyl, sertraline HCl, sevelamer HCl, sevoflurane, silymarin/milk thistle, sodium bicarbonate, sodium polystyrene sulfonate, sodium stibogluconate, sodium sulfate, sodum thiosulfate, somatotropin, sotalol HCl, spectinomycin HCl, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline HCl, terbutaline sulfate, testosterone, tetracycline HCl, thiabendazole, thiacetarsamide sodium, thiamine HCl, thioguanine, thiopental sodium, thiotepa, thyrotropin, tiamulin, ticarcilin disodium, tiletamine HCl/zolazepam HCl, tilmocsin, tiopronin, tobramycin sulfate, tocainide HCl, tolazoline HCl, telfenamic acid, topiramate, tramadol HCl, trimcinolone acetonide, trientine HCl, trilostane, trimepraxine tartrate w/prednisolone, tripelennamine HCl, tylosin, urdosiol, valproic acid, vanadium, vancomycin HCl, vasopressin, vecuronium bromide, verapamil HCl, vinblastine sulfate, vincristine sulfate, vitamin E/selenium, warfarin sodium, xylazine HCl, yohimbine HCl, zafirlukast, zidovudine (AZT), zinc acetate/zinc sulfate, zonisamide and mixtures thereof.

In one embodiment of the invention, other arylpyrazole compounds such as phenylpyrazoles, as described above in the Background (e.g. fipronil), are known in the art and are suitable for combination with the dimeric aryl pyrazole compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (each assigned to Merial, Ltd., Duluth, Ga.).

In another embodiment of the invention, nodulisporic acid and its derivatives (a class of known acaricidal, anthelminitic, anti-parasitic and insecticidal agents) can be added to the compositions of the invention. These compounds are used to treat or prevent infections in humans and animals and are described, for example, in U.S. Pat. Nos. 5,399,582 and 5,962,499. The composition can include one or more of the known nodulisporic acid derivatives in the art, including all stereoisomers, such as those described in the literature cited above.

In another embodiment of the invention, one or more macrocyclic lactones, which act as an acaricide, anthelmintic agent and insecticide, can be added to the compositions of the invention.

The macrocyclic lactones also include, but are not limited to, avermectins, such as abamectin, dimadectin, doramectin, emamectin, eprinomectin, ivermectin, latidectin, lepimectin, selamectin and milbemycins, such as milbemectin, milbemycin D, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131 (each assigned to Merial, Ltd., Duluth, Ga.).

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519, and the 22,23-dihydro avermectin compounds are disclosed in U.S. Pat. No. 4,199,569. Mention is also made of U.S. Pat. Nos. 4,468,390 and 5,824,653, EP 0 007 812 A1, U.K. 1 390 336, EP 0 002 916, and New Zealand Patent No.

237 086, inter alia. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, N.J. (1996). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In another embodiment of the invention, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (both assigned to Merial Ltd., Duluth, Ga.). Examples of IGRs suitable for use include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

An anthelmintic agent that can be combined with the compound of the invention to form a composition can be a benzenedisulfonamide compound, which includes but is not limited to clorsulon; or a cestodal agent, which includes but is not limited to praziquantel, pyrantel or morantel.

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside.

An insecticidal agent that can be combined with the compound of the invention to form a composition can be a spinosyn (e.g. spinosad) or a substituted pyridylmethyl derivative compound such as imidacloprid. Agents of this class are described above, and for example, in U.S. Pat. No. 4,742,060 or EP 0 892 060. It would be well within the skill level of the practitioner to decide which individual compound can be used in the inventive formulation to treat a particular infection of an insect.

In another embodiment, the compositions of the invention may advantageously include one or more compounds of the isoxazoline class of compounds. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment of the invention, nodulisporic acid and its derivatives (a class of known acaricidal, anthelminitic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181. The compositions of the invention may also include aryloazol-2-yl cyanoethylamino compounds such as those described in US 2008/0312272 to Soll et al., which is incorporated herein in its entirety, and thioamide derivatives of these compounds, as described in U.S. patent application Ser. No. 12/582,486, filed Oct. 20, 2009, which is incorporated herein by reference.

The compositions of the invention may also be combined with paraherquamide compounds and derivatives of these compounds, including derquantel (see Ostlind et al., *Research in Veterinary Science,* 1990, 48, 260-61; and Ostlind et al., *Medical and Veterinary Entomology,* 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. No. 5,703,078 and U.S. Pat. No. 5,750,695, all of which are hereby incorporated by reference in their entirety.

In general, the additional active agent is included in a dose of between about 0.1 µg and about 1000 mg. More typically, the additional active agent may be included in a dose of about 10 µg to about 500 mg, about 1 mg to about 300 mg, about 10 mg to about 200 mg or about 10 mg to about 100 mg. In one embodiment of the invention, the additional active agent is included in a dose of between about 1 µg and about 10 mg. In other embodiments of the invention, the additional active agent may be included in a dose of about 5 µg/kg to about 50 mg/kg per weight of the animal. In other embodiments, the additional active agent may be present in a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

The proportions, by weight, of the dimeric aryl pyrazole compound and the additional pesticidal agent are for example between about 5/1 and about 10,000/1. However, one of ordinary skill in the art would be able to select the appropriate ratio of dimeric aryl pyrazole compound and the additional pesticidal agent for the intended host and use thereof.

The compounds of the invention or their salts can be employed as such or in the form of their preparations (formulations) as combinations with other pesticidally active substances, such as, for example, insecticides, attractants, sterilants, acaricides, nematicides, herbicides, fungicides, and with safeners, fertilizers and/or growth regulators, for example as a premix/readymix.

Classifications of fungicides are well-known in the art and include classifications by FRAC (Fungicide Resistance Action Committee). Fungicides which may optionally be admixed include, but are not limited to, methyl benzimidazole carbamates, such as benzimidazoles and thiophanates; dicarboximides; demethylation inhibitors, such as imidazoles, piperazines, pyridines, pyrimidines, and triazoles; phenylamides, such as acylalanines, oxazolidinones, and butyrolactones; amines, such as morpholines, piperidines, and spiroketalamines; phosphorothiolates; dithiolanes; carboxamides; hydroxy-(2-amino-)pyrimidines; anilino-pyrimidines; N-phenyl carbamates; quinone outside inhibitors; phenylpyrroles; quinolines; aromatic hydrocarbons; heteroaromatics; melanin biosynthesis inhibitors-reductase; melanin biosynthesis inhibitors-dehydratase; hydroxyanilides (SBI class III), such as fenhexamid; SBI class IV, such as thiocarbamates and allylamines; polyoxins; phenylureas; quinone inside inhibitors; benzamides; enopyranuronic acid antibiotic; hexopyranosyl antibiotic; glucopyranosyl antibiotic; glucopyranosyl antibiotic; cyanoacetamideoximes; carbamates; uncoupler of oxidative phosphorylation; organo tin compounds; carboxylic acids; heteroaromatics; phosphonates; phthalamic acids; benzotriazines; benzenesulfonamides; pyridazinones; carboxylic acid amides; tetracycline antibiotic; thiocarbamate; benzo-thiadiazole BTH; benzisothiazole; thiadiazolecarboxamide; thiazolecarboxamides; benzamidoxime; quinazolinone; benzophenone; acylpicolide; inorganic compounds, such as copper salts and sulphur; dithiocarbamates and relatives; phthalimides; chloronitriles; sulphamides; guanidines; triazines; quinones. Other fungicides that may optionally be admixed may also be from the classes of compounds described in U.S. Pat. Nos. 7,001,903 and 7,420,062.

Herbicides that are known from the literature and classified by HRAC (Herbicide Resistance Action Committee) and may be combined with the compounds of the invention, are, for example: aryloxyphenoxy-propionate; cyclohexanedione; phenylpyrazoline; sulfonylurea; imidazolinone, such as imazapic and imazethapyr; triazolopyrimidine; pyrimidinyl (thio)benzoate; sulfonylaminocarbonyl-triazolinone; triazine, such as atrazine; triazinone; triazolinone; uracil; pyridazinone; phenyl-carbamate; urea; amide; nitrile; benzothiadiazinone; phenyl-pyridazine; bipyridylium, such as paraquat; diphenylether; phenylpyrazole; N-phenylphthalimide; thiadiazole; thiadiazole; triazolinone; oxazolidinedione; pyrimidindione; pyridazinone; pyridinecarboxamide; triketone; isoxazole; pyrazole; triazole; isoxazolidinone; urea, such as linuron; diphenylether; glycine, such as glyphosate; phosphinic acid, such as glufosinate-ammonium; carbamate; dinitroaniline, such as pendimethalin; phosphoroamidate; pyridine; benzamide; benzoic acid; chloroacetamide; metolachlor; acetamide; oxyacetamide; tetrazolinone; nitrile; benzamide; triazolocarboxamide; quinoline carboxylic acid; dinitrophenol; thiocarbamate; phosphorodithioate; benzofuran; chloro-carbonic-acid; phenoxy-carboxylic-acid, such as 2,4-D; benzoic acid, such as dicamba; pyridine carboxylic acid, such as clopyralid, triclopyr, fluroxypyr and picloram; quinoline carboxylic acid; phthalamate semicarbazone; qrylaminopropionic acid; qrylaminopropionic acid; organoarsenical. Other herbicides that may optionally be admixed are compounds described in U.S. Pat. Nos. 7,432,226, 7,012,041, and 7,365,082. Appropriate herbicide safeners include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anyhydride and oxabetrinil.

Bactericides include, but are not limited to, bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/acaricides/nematicides include those compounds mentioned in U.S. Pat. Nos. 7,420,062 and 7,001,903, U.S. Patent publication 2008/0234331, the literature known to the person skilled in the art, and the compounds classified by IRAC (Insecticide Resistance Action Committee). Examples of insecticides/acaricides/nematicides include, but are limited to, carbamates; triazemate; organophosphates; cyclodiene organochlorines; phenylpyrazoles; DDT; methoxychlor; pyrethroids; pyrethrins; neonicotinoids; nicotine; bensultap; cartap hydrochloride; nereistoxin analogues; spinosyns; avermectins and milbemycins; juvenile hormone analogues; fenoxycarb; fenoxycarb; alkyl halides; chloropicrin; sulfuryl fluoride; cryolite; pymetrozine; flonicamid; clofentezine; hexythiazox; etoxazole; *Bacillus sphaericus*; diafenthiuron; organotin miticides; propargite; tetradifon; chlorfenapyr; DNOC; benzoylureas; buprofezin; cyromazine; diacylhydrazines; azadirachtin; amitraz; hydramethylnon; acequinocyl; fluacrypyrim; METI acaricides; rotenone; indoxacarb; metaflumizone; tetronic acid derivatives; aluminium phosphide; cyanide; phosphine; bifenazate; fluoroacetate; P450-dependent monooxygenase inhibitors; esterase inhibitors; diamides; benzoximate; chinomethionat; dicofol; pyridalyl; borax; tartar emetic; fumigants, such as methyl bromide; ditera; clandosan; sincocin.

The compounds of the invention can be formulated in various ways, depending on the prevailing biological and/or chemico-physical parameters. Examples of possible formulations are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

The formulations aforementioned can be prepared in a manner known, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Wettable powders are preparations which are uniformly dispersible in water and which, in addition to the compounds of the invention also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of the invention are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of the invention in an organic solvent, for example, butanol, cyclohexanone, dimethylformamide, xylene or else higher-boiling aromatics or hydrocarbons or mixture of these, with addition of one or more ionic and/or nonionic surfactants (emulsifiers). Emulsifiers which can be used are, for example, calcium salts of alkylarylsulfonic acids such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters, or polyoxyethylene sorbitan esters such as polyoxyethylene sorbitan fatty acid esters.

Dusts are obtained by grinding the active substance with finely divided solid substances, for example, talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above, for example, in the case of the other formulation types.

Emulsions, for example oil-in-water emulsions (EW), can be prepared by means of stirrers, colloid mills and/or static mixtures using aqueous organic solvents and, if appropriate, surfactants as they have already been mentioned above for example in the case of the other formulation types.

Granules can be prepared either by spraying the compounds of the invention onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired, in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

In general, the agrochemical preparations comprise a range selected from the group consisting of about 0.1 to about 99% by weight and about 0.1 to about 95% by weight, of compounds of the invention.

The concentration of compounds of the invention in wettable powder is, for example, about 10 to about 90% by weight, the remainder to 100% by weight being composed of customary formulation components. In the case of emulsifiable concentrates, the concentration of compounds of the invention can amount to a range selected from the group consisting of about 1% to about 90%, and about 5% to about 80% by weight. Formulations in the form of dusts usually comprise in a range selected from the group consisting of about 1% to about 30%, and about 5% to about 20% by weight of compounds of the invention. Sprayable solutions comprise a range selected from the group consisting of about 0.05% to about 80%, and about 2% to about 50% by weight of compounds of the invention. In the case of water-dispersible granules, the content of compounds of the invention depends partly on whether the compounds of the invention are in liquid or solid form and on which granulation auxiliaries, fillers and the like are being used. The water-dispersible granules, for example, comprise a range selected from the group consisting of between about 1 and about 95%, and between about 10% and about 80% by weight.

In addition, the formulations of compounds of the invention mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The mixtures according to the invention can be applied via the soil either pre-emergently or post-emergently. The mixtures according to the invention can also be applied via the leaf. The mixtures according to the invention can be employed for seed dressing. It is also possible to apply the mixtures according to the invention via an irrigation system, for example, via the water for irrigation.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergistic agent added to be active itself When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

All plants and plant parts can be treated in accordance with the invention. Plants are to be understood as meaning, in the present context, all plants and plant populations such as wild plants or crop plants (including naturally occurring crop plants). Crop plants are plants obtained by conventional plant breeding and optimization methods, or by biotechnological and genetic engineering methods, or by combinations of these methods, which includ transgenic plants and plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example, by immersion, spraying, evaporation, fogging, scattering, painting on, injection and, in the case of propagation material, in particular in the case of seeds, also by applying one or more coats.

The active compounds according to the invention are particularly suitable for treating seed. A large part of the damage to crop plants which is caused by pests occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Protecting the seed and the germinating plant by the use of suitable active compounds is therefore of particularly great interest.

The control of pests by treating the seeds of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection agents being employed.

The present invention therefore also relates to a method for the protection of seed and germinating plants from attack by pests, by treating the seed with an active compound according to the invention. The invention likewise relates to the use of the active compounds according to the invention for the treatment of seed for protecting the seed and the resultant plant from pests. Furthermore, the invention relates to seed which has been treated with an active compound according to the invention so as to afford protection from pests.

One of the advantages of the present invention is that the particular systemic properties of the active compounds according to the invention mean that treatment of the seed with these active compounds not only protects the seed itself, but also the resulting plants after emergence, from pests. In this manner, the immediate treatment of the crop at the time of sowing or shortly thereafter can be dispensed with.

Furthermore, it must be considered as advantageous that the active compounds according to the invention can also be employed in particular in transgenic seed, the plants arising from the seed being capable of expressing a protein directed against pests. By treating such seed with the active compounds according to the invention, certain pests can be controlled merely by the expression of, for example, insecticidal protein, and additionally be protected by the active compounds according to the invention against damage.

The active compounds according to the invention are suitable for protecting seed of any plant variety as already mentioned above which is employed in agriculture, in greenhouse, in forests, or in horticulture. In particular, this takes the form of seed of maize, peanut, canola, oilseed rape, poppy, soya beans, cotton, beet (for example sugar beet and fodder beet), rice, sorghum and millet, wheat, barley, oats, rye, sunflower, tobacco, potatoes or vegetables (for example tomatoes, cabbage plants). The active compounds according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with an active compound according to the invention is also of particular importance. This takes the form of seed of plants which, as a rule, comprise at least one heterologous gene which governs the expression of a polypeptide with particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is suitable for the treatment of transgenic seed which comprises at least one heterologous gene originating from *Bacillus* sp. and whose gene product shows activity against the European corn borer and/or the corn root worm.

In the context of the present invention, the active compound according to the invention is applied to the seed either alone or in a suitable formulation. Preferably, the seed is treated in a state which is stable enough to avoid damage during treatment. In general, the seed may be treated at any point in time between harvest and sowing. The seed used has usually been separated from the plant and is free from cobs, shells, stalks, coats, hairs or the flesh of the fruits.

When treating the seed, care must generally be taken that the amount of the active compound according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

As already mentioned above, it is possible to treat all plants and their parts according to the invention. In one embodiment, wild plant species and plant cultivars, or those obtained by conventional biological breeding methods, such as crossing or protoplast fusion, and parts thereof, are treated. In another embodiment, transgenic plants and plant cultivars obtained by genetic engineering methods, if appropriate in combination with conventional methods, and parts thereof are treated. In yet another embodiment, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in synergistic effects. Thus, it is possible, for example, to achieve the effects of reduced application rates, widening of the activity spectrum, an increase in the activity of the active compounds and compositions which can be used according to the invention, better plant growth, increased tolerance to high or low temperatures, increased tolerance to drought or high soil salt content, increased flowering performance, easier harvesting, accelerated maturation, higher harvest yields, higher quality and/or a higher nutritional value of the harvested products, better storage stability and/or processability of the harvested products.

The transgenic plants or plant cultivars (obtained by genetic engineering) which are preferably to be treated according to the invention include all plants which, by virtue of the genetic modification, received genetic material that imparted particularly advantageous, useful traits to these plants. Examples of such traits are better plant growth, increased tolerance to high or low temperatures, increased tolerance to drought or high soil salt content, increased flowering performance, accelerated maturation, higher harvest yields, higher quality and/or a higher nutritional value of the harvested products, better storage stability and/or processability of harvested products. Further and particularly emphasized examples of such traits are a better defense of the plants against animal and microbial pests, such as insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits include, but are not limited to, increased defense of the plants against insects, arachnids, nematodes and slugs and snails by virtue of toxins formed in the plants, and those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits also include, but are not limited to, increased defense of the plants against fungi, bacteria and viruses by systemic acquired resistance (SAR), systemin, phytoalexins, elicitors and resistance genes and correspondingly expressed proteins and toxins. Traits further include, but are not limited to, increased tolerance of the plants to certain herbicidally active compounds, for example, imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soybean varieties, and potato varieties which are sold under the trade names YIELD GARD® (such as maize, cotton, soybean), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soybean varieties which are sold under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) include the varieties sold under the name Clearfield® (for example maize).

In the field of household insecticides, the active compounds according to the invention are used alone or in combination with other suitable active compounds, such as phosphoric esters, carbamates, pyrethroids, neonicotinoids, growth regulators or active compounds from other known classes of insecticides.

It has furthermore been found that the active compounds according to the invention also have a strong insecticidal action against insects which destroy industrial materials.

The following insects may be mentioned as examples, but without any limitation: beetles, hymenopterons, termites and bristletails.

Industrial materials in the present connection are to be understood as meaning non-living materials, such as, preferably, plastics, adhesives, sizes, papers and cardboards, leather, wood and processed wood products and coating compositions.

The active compounds according to the invention are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The compounds of formulas (I), (II), and (III) may be prepared by the application or adaptation of known methods (i.e. methods heretofore used or described in the chemical literature) or methods described, for example, in one or more of U.S. Pat. Nos. 6,350,771, 6,750,230, 5,232,940, WO 01/32663, and EP 780 378 (U.S. Pat. No. 5,817,688). It will be appreciated by the skilled artisan that other methods which are described in the references cited herein also may be employed. It will also be appreciated by the skilled artisan that the order of the synthetic steps employed may be varied and will depend inter alia on factors such as the nature of other functional groups present in a particular substrate, the availability of key intermediates, and the protecting group strategy (if any) to be adopted (see e.g. "*Protective Groups in Organic Synthesis* ($3^{rd}$ Edition)", Greene and Wuts, ed., Wiley-Interscience, (1999). Clearly, such factors will also influence the choice of reagents for use in the said synthetic steps.

The invention is further described by the following non-limiting examples which further illustrate the invention, and are not intended, nor should they be interpreted to, limit the scope of the invention.

The compounds of formula (I) may be prepared according to, for example, the processes described in Scheme 1. Pyrazole derivatives such as (IV), examples of which are disclosed in EP 0 295 117, may be treated with bromine followed by a metal thiocyanate. Reduction of the thiocyanate may occur in the presence of a base such as a metal borohydride in an alcoholic solvent to generate disulfide (VI). Further exposure of the disulfide to a metal borohydride may provide the thiol (VII). Oxidation of the thiol to obtain the sulfonyl chloride may be achieved using, for instance, trimethylsilyl chloride and an alkali metal nitrate such as potassium nitrate (see, e.g. *Journal of Organic Chemistry* 2007, 72, 5847 and references cited therein). Alternatively, sulfuryl chloride may be used in lieu of trimethylsilyl chloride for the oxidation step. The resultant sulfonyl chloride may then be coupled with a linker (IX) (protected on one end and designated as "PG") containing a terminal amino group to afford (X). Removal of the protecting group may generate the free amine, which may in turn then be further reacted with a second sulfonyl chloride derivative of a 1-aryl pyrazole to generate the dimeric product (I).

Scheme 1. Synthesis of compounds of formula (I).

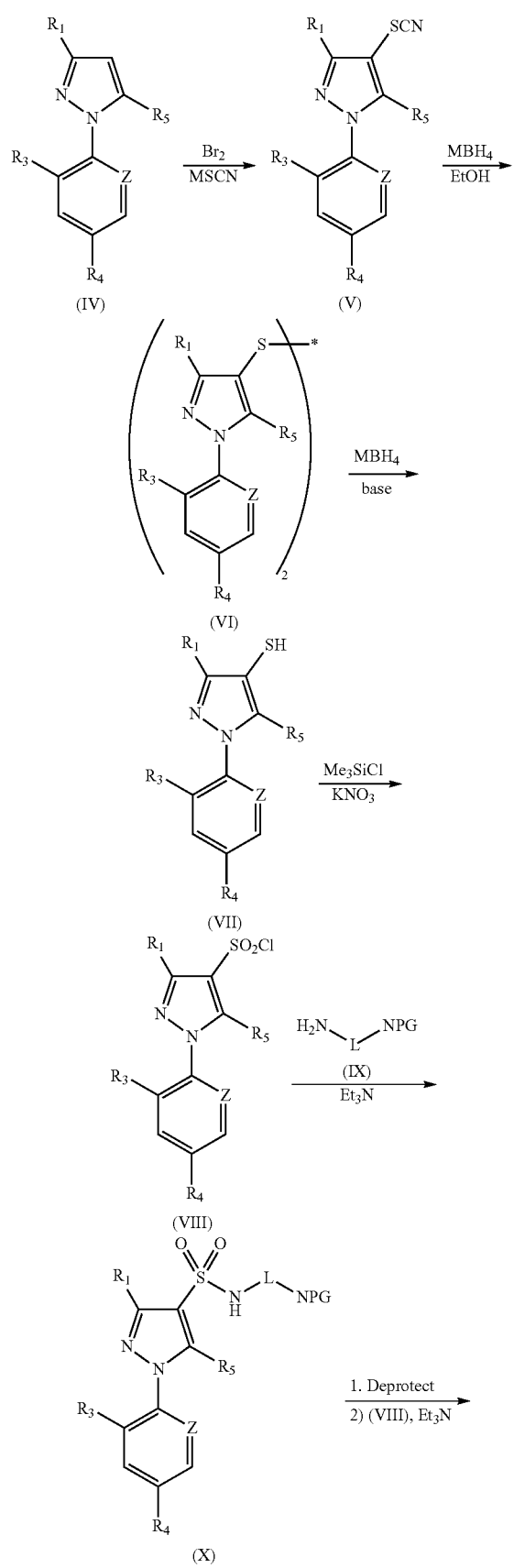

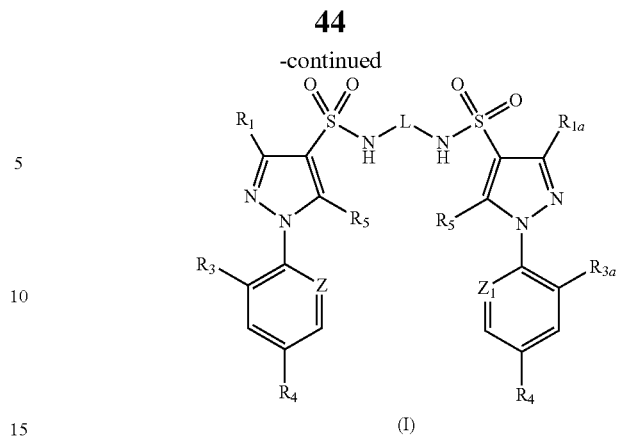

The compounds of formula (IIa) and (IIb) may be prepared according to, for example, the processes described in Scheme 2. 1-Arylpyrazole derivatives such as (XI), which are disclosed for example in EP-A-234,119, may be treated with vinyltributyltin in the presence of a catalyst such as tetrakis(triphenylphosphine)palladium to generate the styryl derivatives (XII). This transformation is recognized in the art as the Stille coupling, a summary of such is found in "*Metal-Catalyzed Cross Coupling Reactions*", F. Diederich and P. J. Stang, Wiley-VCH (1998). The Grubbs' catalyst (vide supra) may be used, for instance, to generate a dimer containing a second arylpyrazole such as (IIa). Optional reduction of the olefin may be achieved via hydrogenation, for example, to provide a saturated linker as in (IIb).

Scheme 2. Synthesis of compounds of formula (IIa) and (IIb).

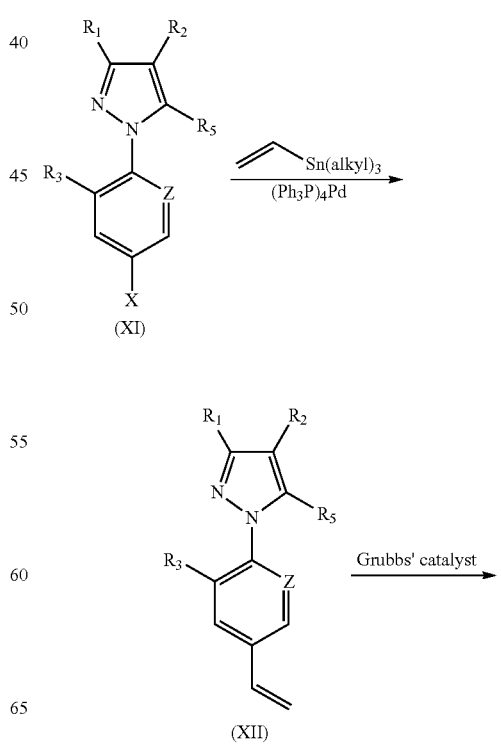

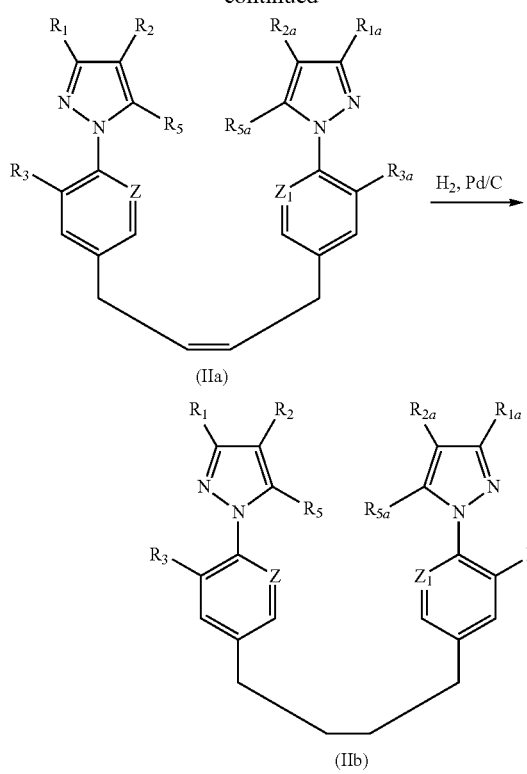

(IIa)

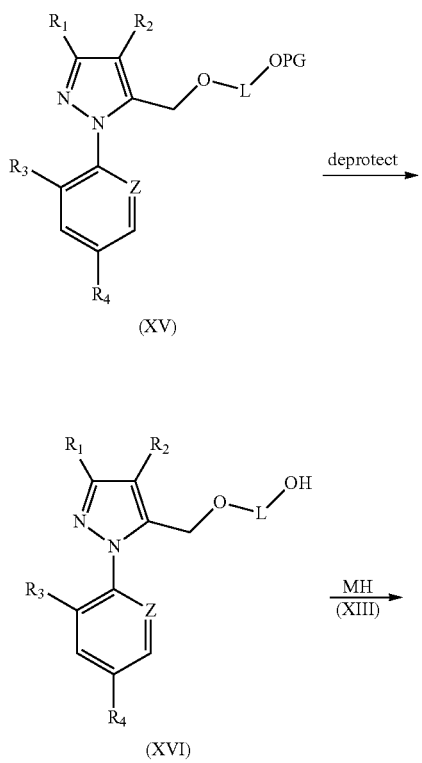

(XV)

(IIb)

(XVI)

The compounds of formula (III) may be prepared according to, for example, the processes described in Schemes 3-5. Halomethyl pyrazole derivatives such as (XIII) may serve as a point of departure, and are disclosed in U.S. application Ser. No. 11/825,050 (Scheme 3). Treatment of a linker (XIV) (protected on one end and designated as "PG") containing a terminal hydroxyl group with a base such as a metal halide may be followed by treatment with (XIII). Removal of the protecting group may generate the free alcohol (XVI), which may then be further reacted with a base such as a metal hydride followed by a second molecule of halomethyl pyrazole to generate the dimeric product (IIIa).

Scheme 3. Synthesis of compounds of formula (III) having linkers containing oxygen.

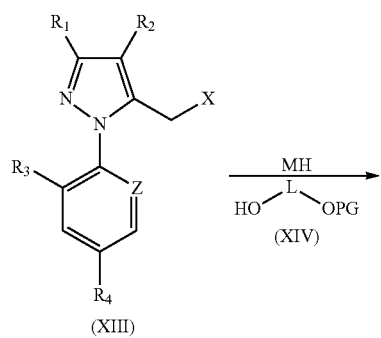

(XIII)

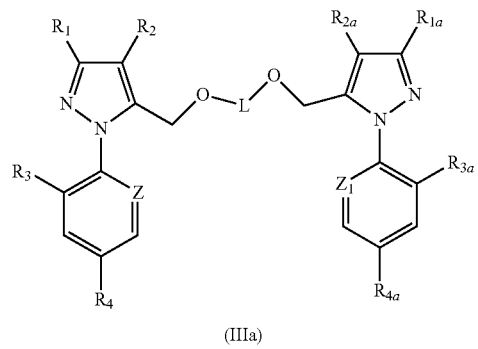

(IIIa)

5-Vinyl pyrazole derivatives such as (XVII), also disclosed in U.S. application Ser. No. 11/825,050, may serve as substrates for the synthesis of compounds of formula (III) containing a carbon linker (Scheme 4). Treatment of (XVII) with a ruthenium-based metathesis reagent such as benzylidene[1,3-bis(2,4,6-trimethylphenyl)-2-imidazolidinylidene]dichloro(tricyclohexylphosphine)ruthenium (commonly referred to in the art as "Grubbs' catalyst", see e.g. *Organic Letters* 2002, 4, 803; 1999, 1, 953 and 1751; and references cited therein) may generate the dimeric product (IIIb). Conversion to the saturated derivative may optionally be achieved via reduction with an appropriate hydrogen source to obtain dimeric product (IIIc).

Scheme 4. Synthesis of compounds of formula (III) having linkers containing carbon.

Scheme 5. Synthesis of compounds of formula (III) having linkers containing ureas.

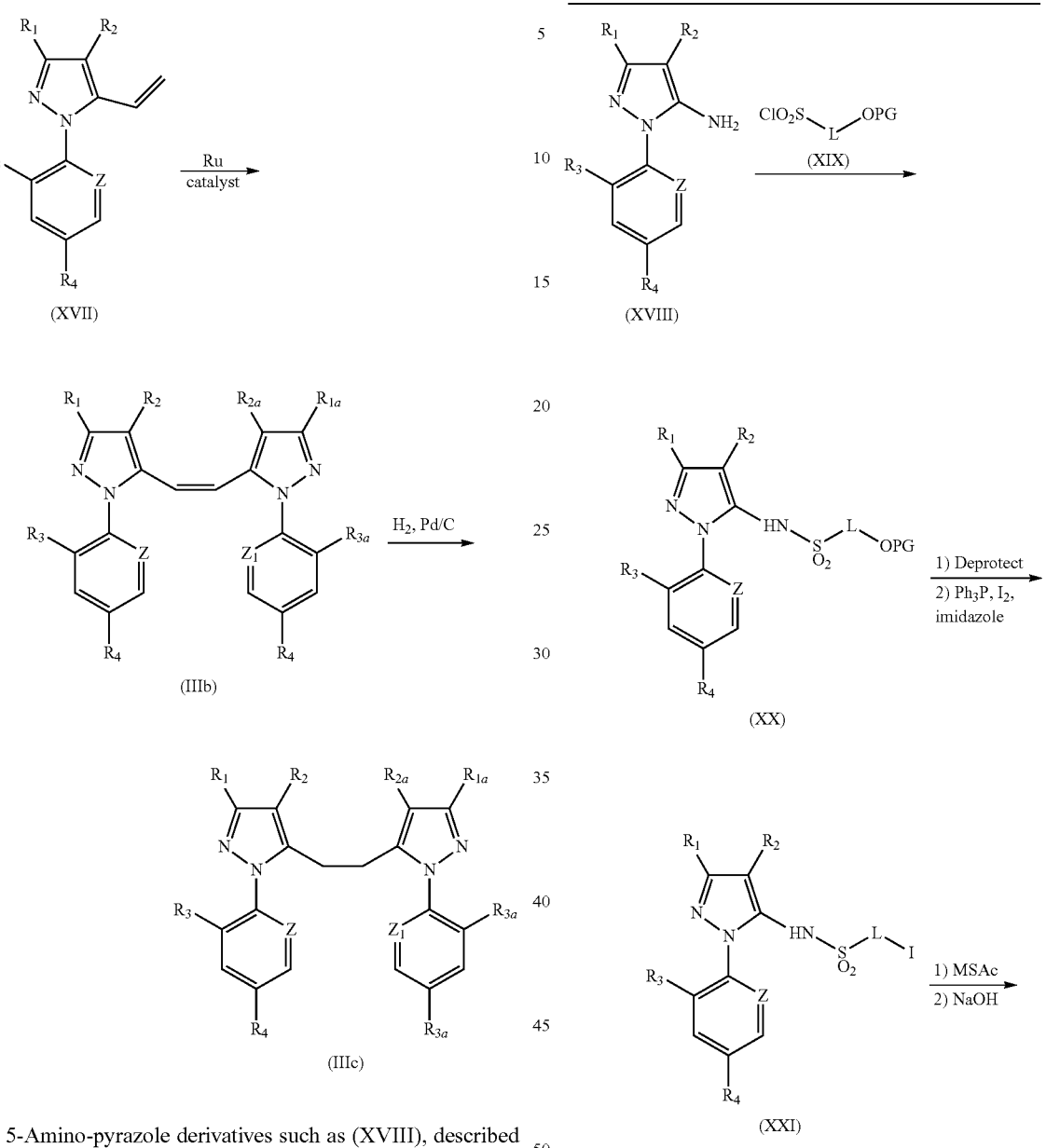

5-Amino-pyrazole derivatives such as (XVIII), described for example in U.S. Pat. Nos. 5,232,940 and 6,346,542, may serve as substrates for the synthesis of compounds of formula (III) containing a amine-based linker (Scheme 5). Treatment of (XVIII) with an appropriately protected linker containing a terminal sulfonyl chloride such as (XIX) may generate a sulfonamide such as (XX). Following removal of the protecting group, conversion of the resultant alcohol to a halide may provide (XXI). Displacement of the halide may be performed via a thioacetate, which may subsequently be converted into a free thiol (XXII). Oxidation to the sulfonyl chloride may be achieved via an alkali metal nitrate in the presence of trimethylsilyl chloride, for example, followed by treatment with a second 5-amino-pyrazole to provide the bis-sulfonamide linked dimer (IIId).

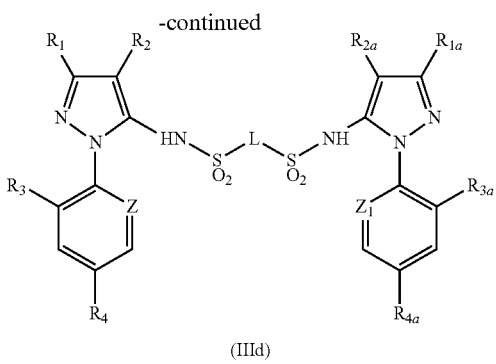

(IIId)

The acids, bases, additives, temperatures, and solvents used in the invention will be apparent to those of ordinary skill in the art (e.g. *Comprehensive Organic Transformations*, R. C. Larock, VCH Publishers (1989); *Vogel's Textbook of Practical Organic Chemistry* ($5^{th}$ Edition), Furniss et al., Longman Scientific & Technical (1989); *Protective Groups in Organic Synthesis* ($3^{rd}$ Edition), Greene & Wuts, Wiley Interscience (1999); *March's Advanced Organic Chemistry: Reactions, Mechanisms, and Structure* ($6^{th}$ Edition), March & Smith, Wiley, (2007); *Advanced Organic Chemistry (Part A—Structure and Mechanisms—$4^{th}$ Edition)*, Carey & Sundberg, Springer Science (2000); *Advanced Organic Chemistry (Part B—Reaction and Synthesis—$4^{th}$ Edition)*, Carey & Sundberg, Springer Science (2001); *Strategic Applications of Named Reactions in Organic Synthesis*, Kurti and Czako, Academic Press (2005).

The invention is also directed toward a method of treating an animal (e.g. a mammal or bird) against ectoparasitic infection by administering an ectoparasiticidally effective amount of the composition of the invention. Mammals which can be treated include but are not limited to humans, cats, dogs, cattle, chickens, cows, deer, goats, horses, llamas, pigs, sheep and yaks. In one embodiment of the invention, the mammals treated are humans, cats or dogs.

In another embodiment for treatment against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes*, and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felis, Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheyletiella* sp., *Lignonathus* sp., and the like), mosquitoes (*Aedes* sp., *Culex* sp., *Anopheles* sp., and the like) and flies (*Hematobia* sp., *Musca* sp., *Stomoxys* sp., *Dematobia* sp., *Cochliomyia* sp., and the like). In yet another embodiment for the treatment against ectoparasites, the ectoparasite is a flea and/or tick.

Additional examples of ectoparasites include but are not limited to the tick genus *Boophilus*, especially those of the species *microplus* (cattle tick), *decoloratus* and *annulatus*; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabici* and *Psoroptes ovis*. The above list is not exhaustive and other ectoparasites are well known in the art to be harmful to animals and humans. These include, for example migrating dipterous larvae.

When an anthelmintic agent is added to the composition of the invention, the composition can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris*, and *Trichostrongylus*.

In another embodiment of the invention, the compounds and compositions of the invention are suitable for controlling pests such as insects selected from the group consisting of *Blatella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the invention can also be used to treat other pests which include but are not limited to pests:

(1) from the order of Isopoda, for example *Oniscus asellus, Armadillidium vulgare* and *Porcellio scaber*;

(2) from the order of Diplopoda, for example *Blaniulus guttulatus*;

(3) from the order of Chilopoda, for example *Geophilus carpophagus* and *Scutigera* spp.;

(4) from the order of Symphyla, for example *Scutigerella immaculata*;

(5) from the order of Thysanura, for example *Lepisma saccharina*;

(6) from the order of Collembola, for example *Onychiurus armatus*;

(7) from the order of Blattaria, for example *Blatta orientalis, Periplaneta americana, Leucophaea maderae* and *Blattella germanica*;

(8) from the order of Hymenoptera, for example *Diprion* spp., *Hoplocampa* spp., *Lasius* spp., *Monomorium pharaonis* and *Vespa* spp.;

(9) from the order of Siphonaptera, for example *Xenopsylla cheopis* and *Ceratophyllus* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipi-*

*cephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici.;*

(12) from the class of Bivalva, for example, *Dreissena* spp.;

(13) from the order of Coleoptera, for example, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apogonia* spp., *Atomaria* spp., *Attagenus* spp., *Bruchidius obtectus*, *Bruchus* spp., *Ceuthorhynchus* spp., *Cleonus mendicus*, *Conoderus* spp., *Cosmopolites* spp., *Costelytra zealandica*, *Curculio* spp., *Cryptorhynchus lapathi*, *Dermestes* spp., *Diabrotica* spp., *Epilachna* spp., *Faustinus cubae*, *Gibbium psylloides*, *Heteronychus arator*, *Hylamorpha elegans*, *Hylotrupes bajulus*, *Hypera postica*, *Hypothenemus* spp., *Lachnosterna consanguinea*, *Leptinotarsa decemlineata*, *Lissorhoptrus oryzophilus*, *Lixus* spp., *Lyctus* spp., *Meligethes aeneus*, *Melolontha melolontha*, *Migdolus* spp., *Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popillia japonica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Sternechus* spp., *Symphyletes* spp., *Tenebrio molitor*, *Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.;

(15) from the class of Gastropoda, for example, *Anion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti.;*

(17) from the order of Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.;

(18) from the order of Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma pini*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona manginata*, *Carneocephala fulgida*, *Ceratovacuna lanigera*, *Cencopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus nibis*, *Dalbulus* spp., *Dialeunodes* spp., *Diaphorina* spp., *Diaspis* spp., *Dorsalis* spp., *Drosicha* spp., *Dysaphis* spp., *Dysmicoccus* spp., *Empoasca* spp., *Eniosoma* spp., *Erythroneura* spp., *Euscelis bilobatus*, *Geococcus coffeae*, *Homalodisca coagulata*, *Hyalopterus anundinis*, *Icenya* spp., *Idiocenus* spp., *Idioscopus* spp., *Laodelphax striatellus*, *Lecanium* spp., *Lepidosaphes* spp., *Lipaphis enysimi*, *Macnosiphum* spp., *Mahanarva fimbriolata*, *Melanaphis sacchani*, *Metcalfiella* spp., *Metopolophium dinhodum*, *Monellia costalis*, *Monelliopsis pecanis*, *Myzus* spp., *Nasonovia nibisnigni*, *Nephotettix* spp., *Nilaparvata lugens*, *Oncometopia* spp., *Onthezia praelonga*, *Panabemisia mynicae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii.;*

(19) from the order of Isoptera, for example, *Reticulitermes* spp., *Odontotermes* spp.;

(20) from the order of Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.;

(21) from the order of Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria.;*

(22) from the order of Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.;

(23) from the class of Protozoa, for example, *Eimeria* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

In each aspect of the invention, the compounds and compositions of the invention can be applied against a single pest or combinations thereof.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development.

The invention is further described by the following numbered paragraphs:

(1) A compound of formula (I):

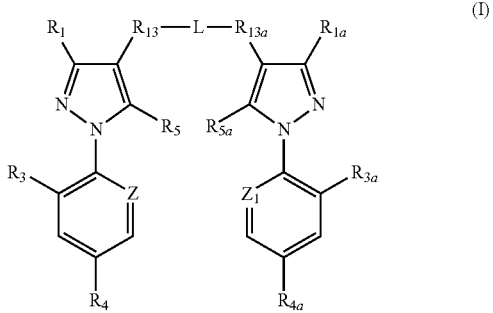

wherein:

$R_1$ and $R_{1a}$ are independently selected from the group consisting of hydrogen, cyano, halogen, $R_6$, —C(=O)$R_6$, —C(=O)$R_8$, —C(=O)NR$_{11}$R$_{12}$, —CH(=NR$_7$), —CH(=NR$_8$), —C(=NR$_7$)R$_7$, —C(=NR$_7$)R$_8$, —C(=NR$_8$)R$_7$, —C(=NNR$_7$)R$_7$, —C(=NNR$_7$)R$_8$, —C(=NNR$_8$)R$_7$, and —C(S)NR$_7$R$_{11}$;

$R_3$ and $R_{3a}$ are independently selected from the group consisting of hydrogen, halogen, cyano, nitro, alkyl, cycloalkyl, haloalkyl, alkoxy, and haloalkoxy;

$R_4$ and $R_{4a}$ are independently selected from the group consisting of halogen, cyano, nitro, $R_7$, $R_8$, —C(O)R$_{11}$, —C(=O)NR$_{11}$R$_{12}$, —C(=NR$_7$)R$_7$, —C(=NR$_7$)R$_8$, —C(=NR$_7$)NR$_{11}$R$_{12}$, —S(O)—R$_{11}$, and SF$_5$;

$R_5$ and $R_{5a}$ are independently selected from the group consisting of $R_{10}$, $R_{11}$, —C(=NR$_7$)R$_7$, —C(=NR$_7$)R$_8$, —C(=NR$_8$)R$_7$, —C(=NR$_7$)NR$_{11}$R$_{12}$, —C(=S)NR$_{11}$R$_{12}$, —NR$_{11}$R$_{12}$, —NR$_{11}$C(=O)R$_8$, —NR$_{11}$C(=O)R$_{11}$, and —N=C(R$_{11}$)NR$_6$;

Z and $Z_1$ are independently selected from the group consisting of a nitrogen atom and C—R$_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and $R_6$;

$R_8$ is selected from the group consisting of —OR$_9$, —OR$_{11}$, —SR$_9$, —SR$_{11}$, —NR$_9$R$_{11}$, and —NR$_{11}$R$_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

$R_{11}$ and $R_{12}$ are independently selected from the group consisting of hydrogen, alkyl, haloalkyl, cycloalkyl, halocycloalkyl, alkenyl, haloalkenyl, alkynyl, and haloalkynyl;

$R_{13}$ and $R_{13a}$ are independently selected from the group consisting of a bond, —O—, —NR$_{11}$—, —NR$_{11}$C(=O)—, —NR$_{11}$C(=S)—, —NR$_{11}$C(=O)O—, —NR$_{11}$C(=O)NR$_{11}$—, —NR$_{11}$C(=S)NR$_{11}$—, —NR$_{11}$SO$_2$NR$_{11}$—, —NR$_{11}$SO$_2$—, —C(=NR$_7$)—, —C(=NR$_8$)—, —C(=O)—, —C(=O)NR$_{11}$—, —C(=S)NR$_{11}$—, —S(O)—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(2) The compound of paragraph (1), wherein:

$R_1$ and $R_{1a}$ are independently selected from the group consisting of hydrogen, cyano, halogen, $R_6$, —C(=O)R$_6$, —C(=O)R$_8$, —C(=O)NR$_{11}$R$_{12}$, —CH(=NR$_7$), —CH(=NR$_8$), —C(=NR$_7$)R$_7$, —C(=NR$_7$)R$_8$, —C(=NR$_8$)R$_7$, and —C(S)NR$_7$R$_{11}$;

$R_3$ and $R_{3a}$ are independently selected from the group consisting of hydrogen, halogen, alkyl, cycloalkyl, haloalkyl, alkoxy, and haloalkoxy;

$R_4$ and $R_{4a}$ are independently selected from the group consisting of halogen, $R_7$, $R_8$, —S(O)$_n$R$_{11}$, and SF$_5$;

$R_5$ and $R_{5a}$ are independently selected from the group consisting of $R_{10}$, $R_{11}$, —C(=NR$_7$)R$_7$, —C(=NR$_7$)R$_8$, —C(=NR$_8$)R$_7$, —C(=NR$_7$)NR$_{11}$R$_{12}$, —C(=S)NR$_{11}$R$_{12}$, —NR$_{11}$R$_{12}$, and —N=C(R$_{11}$)NR$_6$;

Z and $Z_1$ are C—R$_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

R$_7$ is selected from the group consisting of H and R$_6$;

R$_8$ is selected from the group consisting of —OR$_9$, —OR$_{11}$, —SR$_9$, —SR$_{11}$, —NR$_9$R$_{11}$, and —NR$_{11}$R$_{12}$;

R$_9$ is selected from the group consisting of aryl and heteroaryl, wherein said aryl and heteroaryl groups are optionally substituted with one or more groups independently selected from the group consisting of R$_{10}$ and R$_{11}$;

R$_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)—R$_{11}$, —NR$_{11}$S(O)—NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

R$_{11}$ and R$_{12}$ are independently selected from the group consisting of hydrogen, alkyl, haloalkyl, cycloalkyl, halocycloalkyl, alkenyl, haloalkenyl, alkynyl, and haloalkynyl;

R$_{13}$ and R$_{13a}$ are independently selected from the group consisting of a —C(=NR$_7$)—, —C(=NR$_8$)—, —C(=O)—, —C(=O)NR$_{11}$—, —C(=S)NR$_{11}$—, —S(O)—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(3) The compound of paragraph (1), wherein:

R$_1$ and R$_{1a}$ are independently selected from the group consisting of cyano, halogen, and —C(S)NR$_7$R$_{11}$;

R$_3$ and R$_{3a}$ are halogen;

R$_4$ and R$_{4a}$ are independently selected from the group consisting of halogen, haloalkyl, —S(O)$_n$R$_{11}$, and SF$_5$;

R$_5$ and R$_{5a}$ are independently selected from the group consisting of alkyl, haloalkyl, —NR$_{11}$R$_{12}$, and —N=C(R$_{11}$)NR$_6$;

Z and Z$_1$ are C—R$_3$;

R$_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of R$_8$, R$_9$ and R$_{10}$;

R$_7$ is selected from the group consisting of H and alkyl;

R$_8$ is selected from the group consisting of —OR$_9$, —OR$_{11}$, —SR$_9$, —SR$_{11}$, —NR$_9$R$_{11}$, and —NR$_{11}$R$_{12}$;

R$_9$ is selected from the group consisting of aryl and heteroaryl, wherein said aryl and heteroaryl groups are optionally substituted with one or more groups independently selected from the group consisting of R$_{10}$ and R$_{11}$;

R$_{10}$ is selected from the group consisting of cyano, nitro, hydroxyl, halogen, alkyl, cycloalkyl, haloalkyl, alkoxy, haloalkoxy, —S(O)—R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

R$_{11}$ and R$_{12}$ are independently selected from the group consisting of hydrogen, alkyl, and haloalkyl;

R$_{13}$ and R$_{13a}$ are independently selected from the group consisting of a —C(=NR$_7$)—, —C(=NR$_8$)—, —C(=O)—, —C(=O)NR$_{11}$—, —C(=S)NR$_{11}$—, —S(O)$_n$—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(4) The compound of paragraph (1), wherein:

R$_1$ and R$_{1a}$ are independently selected from the group consisting of cyano, and —C(S)NR$_7$R$_{11}$;

R$_3$ and R$_{3a}$ are halogen;

R$_4$ and R$_{4a}$ are haloalkyl;

R$_5$ and R$_{5a}$ are independently selected from the group consisting of alkyl, and —NR$_{11}$R$_{12}$;

Z and Z$_1$ are C—R$_3$;

R$_7$ is selected from the group consisting of H and alkyl;

R$_{11}$ and R$_{12}$ are hydrogen;

R$_{13}$ and R$_{13a}$ are —S(O)$_n$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(5) The compound of paragraph (1), wherein:

R$_1$ and R$_{1a}$ are cyano;

R$_3$ and R$_{3a}$ are halogen;

R$_4$ and R$_{4a}$ are haloalkyl;

R$_5$ and R$_{5a}$ are independently selected from the group consisting of alkyl, and —NR$_{11}$R$_{12}$;

Z and Z$_1$ are C—R$_3$;

R$_{11}$ and R$_{12}$ are hydrogen;

R$_{13}$ and R$_{13a}$ are —S(O)$_n$—;

L is alkyl or haloalkyl; and n is 2; or a salt thereof.

(6) A compound of formula (II):

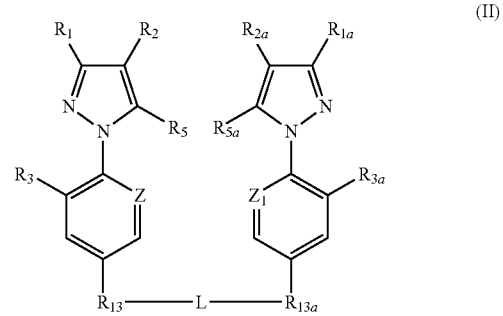

wherein:

R$_1$ and R$_{1a}$ are independently selected from the group consisting of hydrogen, cyano, halogen, R$_6$, —C(=O)R$_6$, —C(=O)R$_8$, —C(=O)NR$_{11}$R$_{12}$, —CH(=NR$_7$), —CH(=NR$_8$), —C(=NR$_7$)R$_7$, —C(=NR$_7$)R$_8$, —C(=NR$_8$)R$_7$, —C(=NNR$_7$)R$_7$, —C(=NNR$_7$)R$_8$, —C(=NNR$_8$)R$_7$, and —C(S)NR$_7$R$_{11}$;

R$_2$ and R$_{2a}$ are independently selected from the group consisting of S(O)$_n$R$_{11}$, and 4,5-dicyanoimidazol-2-yl;

R$_3$ and R$_{3a}$ are independently selected from the group consisting of hydrogen, halogen, cyano, nitro, alkyl, cycloalkyl, haloalkyl, alkoxy, and haloalkoxy;

R$_5$ and R$_{5a}$ are independently selected from the group consisting of R$_{10}$, R$_{11}$, —C(=NR$_7$)R$_7$, —C(=NR$_7$)R$_8$, —C(=NR$_8$)R$_7$, —C(=NR$_7$)NR$_{11}$R$_{12}$, —C(=S)NR$_{11}$R$_{12}$, —NR$_{11}$R$_{12}$, —NR$_{11}$C(=O)R$_8$, —NR$_{11}$C(=O)R$_{11}$, and —N=C(R$_{11}$)NR$_6$;

Z and Z$_1$ are independently selected from the group consisting of a nitrogen atom and C—R$_3$;

R$_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of R$_8$, R$_9$ and R$_{10}$;

R$_7$ is selected from the group consisting of H and R$_6$;

R$_8$ is selected from the group consisting of —OR$_9$, —OR$_{11}$, —SR$_9$, —SR$_{11}$, —NR$_9$R$_{11}$, and —NR$_{11}$R$_{12}$;

R$_9$ is selected from the group consisting of aryl and heteroaryl, wherein said aryl and heteroaryl groups are optionally substituted with one or more groups independently selected from the group consisting of R$_{10}$ and R$_{11}$;

R$_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

R$_{11}$ and R$_{12}$ are independently selected from the group consisting of hydrogen, alkyl, haloalkyl, cycloalkyl, halocycloalkyl, alkenyl, haloalkenyl, alkynyl, and haloalkynyl;

R$_{13}$ and R$_{13a}$ are independently selected from the group consisting of a bond, —O—, —NR$_{11}$—, —NR$_{11}$C(=O)—, —NR$_{11}$C(=S)—, —NR$_{11}$C(=O)O—, —NR$_{11}$C(=O)NR$_{11}$—, —NR$_{11}$C(=S)NR$_{11}$—, —NR$_{11}$SO$_2$NR$_{11}$—, —NR$_{11}$SO$_2$—, —C(=NR$_7$)—, —C(=NR$_8$)—, —C(=O)—, —C(=O)NR$_{11}$—, —C(=S)NR$_{11}$—, —S(O)$_n$—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(7) The compound of paragraph (6), wherein:

R$_1$ and R$_{1a}$ are independently selected from the group consisting of hydrogen, cyano, halogen, R$_6$, —C(=O)R$_6$, —C(=O)R$_8$, —C(=O)NR$_{11}$R$_{12}$, —CH(=NR$_7$), —CH(=NR$_8$), —C(=NR$_7$)R$_7$, —C(=NR$_7$)R$_8$, —C(=NR$_8$)R$_7$, and —C(S)NR$_7$R$_{11}$;

R$_2$ and R$_{2a}$ are independently selected from the group consisting of S(O)$_n$R$_{11}$, and 4,5-dicyanoimidazol-2-yl;

R$_3$ and R$_{3a}$ are independently selected from the group consisting of hydrogen, halogen, alkyl, cycloalkyl, haloalkyl, alkoxy, and haloalkoxy;

R$_5$ and R$_{5a}$ are independently selected from the group consisting of R$_{10}$, R$_{11}$, —C(=NR$_7$)R$_7$, —C(=NR$_7$)R$_8$, —C(=NR$_8$)R$_7$, —C(=NR$_7$)NR$_{11}$R$_{12}$, —C(=S)NR$_{11}$R$_{12}$, —NR$_{11}$R$_{12}$, and —N=C(R$_{11}$)NR$_6$;

Z and Z$_1$ are C—R$_3$;

R$_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of R$_8$, R$_9$ and R$_{10}$;

R$_7$ is selected from the group consisting of H and R$_6$;

R$_8$ is selected from the group consisting of —OR$_9$, —OR$_{11}$, —SR$_9$, —SR$_{11}$, —NR$_9$R$_{11}$, and —NR$_{11}$R$_{12}$;

R$_9$ is selected from the group consisting of aryl and heteroaryl, wherein said aryl and heteroaryl groups are optionally substituted with one or more groups independently selected from the group consisting of R$_{10}$ and R$_{11}$;

R$_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

R$_{11}$ and R$_{12}$ are independently selected from the group consisting of hydrogen, alkyl, haloalkyl, cycloalkyl, halocycloalkyl, alkenyl, haloalkenyl, alkynyl, and haloalkynyl;

R$_{13}$ and R$_{13a}$ are independently selected from the group consisting of a bond, —O—, —S(O)—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(8) The compound of paragraph (6), wherein:

R$_1$ and R$_{1a}$ are independently selected from the group consisting of cyano, halogen, and —C(S)NR$_7$R$_{11}$;

R$_2$ and R$_{2a}$ are independently selected from the group consisting of S(O)$_n$R$_{11}$, and 4,5-dicyanoimidazol-2-yl;

R$_3$ and R$_{3a}$ are halogen;

R$_5$ and R$_{5a}$ are independently selected from the group consisting of alkyl, haloalkyl, —NR$_{11}$R$_{12}$, and —N=C(R$_{11}$)NR$_6$;

Z and Z$_1$ are C—R$_3$;

R$_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of R$_8$, R$_9$ and R$_{10}$;

R$_7$ is selected from the group consisting of H and alkyl;

R$_8$ is selected from the group consisting of —OR$_9$, —OR$_{11}$, —SR$_9$, —SR$_{11}$, —NR$_9$R$_{11}$, and —NR$_{11}$R$_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

$R_{11}$ and $R_{12}$ are independently selected from the group consisting of hydrogen, alkyl, and haloalkyl;

$R_{13}$ and $R_{13a}$ are independently selected from the group consisting of a bond, —O—, —S(O)$_n$—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(9) The compound of paragraph (6), wherein:

$R_1$ and $R_{1a}$ are independently selected from the group consisting of cyano, and —C(S)NR$_7$R$_{11}$;

$R_2$ and $R_{2a}$ are independently selected from the group consisting of S(O)$_n$R$_{11}$, and 4,5-dicyanoimidazol-2-yl;

$R_3$ and $R_{3a}$ are halogen;

$R_5$ and $R_{5a}$ are independently selected from the group consisting of alkyl, and —NR$_{11}$R$_{12}$;

Z and $Z_1$ are C—R$_3$;

$R_7$ is selected from the group consisting of H and alkyl;

$R_{11}$ and $R_{12}$ are independently selected from the group consisting of hydrogen, alkyl, and haloalkyl;

$R_{13}$ and $R_{13a}$ are independently selected from the group consisting of a bond and —S(O)$_n$—; L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(10) The compound of paragraph (6), wherein:

$R_1$ and $R_{1a}$ are cyano;

$R_2$ and $R_{2a}$ are independently selected from the group consisting of S(O)$_n$R$_{11}$, and 4,5-dicyanoimidazol-2-yl;

$R_3$ and $R_{3a}$ are halogen;

$R_4$ and $R_{4a}$ are haloalkyl;

$R_5$ and $R_{5a}$ are independently selected from the group consisting of alkyl, and —NR$_{11}$R$_{12}$;

Z and $Z_1$ are C—R$_3$;

$R_{11}$ and $R_{12}$ are independently selected from the group consisting of hydrogen, alkyl, and haloalkyl;

$R_{13}$ and $R_{13a}$ are a bond;

L is alkyl or haloalkyl; and n is 2; or a salt thereof.

(11) A compound of formula (III):

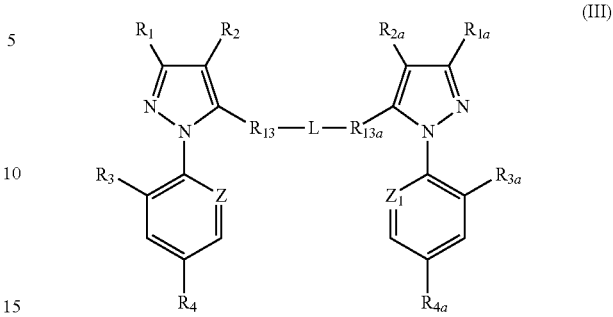

wherein:

$R_1$ and $R_{1a}$ are independently selected from the group consisting of hydrogen, cyano, halogen, $R_6$, —C(=O)R$_6$, —C(=O)R$_8$, —C(=O)NR$_{11}$R$_{12}$, —CH(=NR$_7$), —CH(=NR$_8$), —C(=NR$_7$)R$_7$, —C(=NR$_7$)R$_8$, —C(=NR$_8$)R$_7$, —C(=NNR$_7$)R$_7$, —C(=NNR$_7$)R$_8$, —C(=NNR$_8$)R$_7$, and —C(S)NR$_7$R$_{11}$;

$R_2$ and $R_{2a}$ are independently selected from the group consisting of S(O)$_n$R$_{11}$, and 4,5-dicyanoimidazol-2-yl;

$R_3$ and $R_{3a}$ are independently selected from the group consisting of hydrogen, halogen, cyano, nitro, alkyl, cycloalkyl, haloalkyl, alkoxy, and haloalkoxy;

$R_4$ and $R_{4a}$ are independently selected from the group consisting of halogen, cyano, nitro, $R_7$, $R_8$, —C(O)R$_{11}$, —C(=O)NR$_{11}$R$_{12}$, —C(=NR$_7$)R$_7$, —C(=NR$_7$)R$_8$, —C(=NR$_7$)NR$_{11}$R$_{12}$, —S(O)$_n$R$_{11}$, and SF$_5$;

Z and $Z_1$ are independently selected from the group consisting of a nitrogen atom and C—R$_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and $R_6$;

$R_8$ is selected from the group consisting of —OR$_9$, —OR$_{11}$, —SR$_9$, —SR$_{11}$, —NR$_9$R$_{11}$, and —NR$_{11}$R$_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)R$_{11}$, —NR$_{11}$(C=O)NR$_{11}$R$_{12}$, —NR$_{11}$S(O)—R$_{11}$, —NR$_{11}$S(O)—NR$_{11}$R$_{12}$, —C(=O)R$_{11}$, —C(=O)OR$_{11}$, —C(=O)NR$_{11}$R$_{12}$, —C(=S)R$_{11}$, —C(=S)NR$_{11}$R$_{12}$;

$R_{11}$ and $R_{12}$ are independently selected from the group consisting of hydrogen, alkyl, haloalkyl, cycloalkyl, halocycloalkyl, alkenyl, haloalkenyl, alkynyl, and haloalkynyl;

$R_{13}$ and $R_{13a}$ are independently selected from the group consisting of a bond, —O—, —NR$_{11}$SO$_2$NR$_{11}$—, —NR$_{11}$SO$_2$—, —C(=NR$_7$)—, —C(=NR$_8$)—, —C(=O)—, —C(=O)NR$_{11}$—, —C(=S)NR$_{11}$—, —C(=NR$_7$)NR$_{11}$, —S(O)$_n$—, and —S(O)$_n$NR$_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(12) The compound of paragraph (11), wherein:

$R_1$ and $R_{1a}$ are independently selected from the group consisting of hydrogen, cyano, halogen, $R_6$, —C(=O)$R_6$, —C(=O)$R_8$, —C(=O)$NR_{11}R_{12}$, —CH(=$NR_7$), —CH(=$NR_8$), —C(=$NR_7$)$R_7$, —C(=$NR_7$)$R_8$, —C(=$NR_8$)$R_7$, and —C(S)$NR_7R_{11}$;

$R_2$ and $R_{2a}$ are independently selected from the group consisting of S(O)$_n$$R_{11}$, and 4,5-dicyanoimidazol-2-yl;

$R_3$ and $R_{3a}$ are independently selected from the group consisting of hydrogen, halogen, alkyl, cycloalkyl, haloalkyl, alkoxy, and haloalkoxy;

$R_4$ and $R_{4a}$ are independently selected from the group consisting of halogen, $R_7$, $R_8$, —S(O)$_n$$R_{11}$, and $SF_5$;

Z and $Z_1$ are C—$R_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and $R_6$;

$R_8$ is selected from the group consisting of —$OR_9$, —$OR_{11}$, —$SR_9$, —$SR_{11}$, —$NR_9R_{11}$, and —$NR_{11}R_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —S(O)$_n$$R_{11}$, —S(O)$_n$$NR_{11}R_{12}$, —$NR_{11}R_{12}$, —$NR_{11}$(C=O)$R_{11}$, —$NR_{11}$(C=O)$NR_{11}R_{12}$, —$NR_{11}$S(O)$_n$$R_{11}$, —$NR_{11}$S(O)$_n$$NR_{11}R_{12}$, —C(=O)$R_{11}$, —C(=O)$OR_{11}$, —C(=O)$NR_{11}R_{12}$, —C(=S)$R_{11}$, —C(=S)$NR_{11}R_{12}$;

$R_{11}$ and $R_{12}$ are independently selected from the group consisting of hydrogen, alkyl, haloalkyl, cycloalkyl, halocycloalkyl, alkenyl, haloalkenyl, alkynyl, and haloalkynyl;

$R_{13}$ and $R_{13a}$ are independently selected from the group consisting of a bond, —O—, —$NR_{11}SO_2NR_{11}$—, —$NR_{11}SO_2$—, —C(=$NR_7$)—, —C(=$NR_8$)—, —C(=O)—, —C(=O)$NR_{11}$—, —C(=S)$NR_{11}$—, —C(=$NR_7$)$NR_{11}$, —S(O)$_n$—, and —S(O)$_n$$NR_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(13) The compound of paragraph (11), wherein:

$R_1$ and $R_{1a}$ are independently selected from the group consisting of cyano, halogen, and —C(S)$NR_7R_{11}$;

$R_2$ and $R_{2a}$ are independently selected from the group consisting of S(O)$_n$$R_{11}$, and 4,5-dicyanoimidazol-2-yl;

$R_3$ and $R_{3a}$ are halogen;

$R_4$ and $R_{4a}$ are independently selected from the group consisting of halogen, haloalkyl, —S(O)$_n$$R_{11}$, and $SF_5$;

Z and $Z_1$ are C—$R_3$;

$R_6$ is selected from the group consisting of alkyl, haloalkyl, cycloalkyl, halocycloalkyl, alkenyl, alkynyl, aryl and heteroaryl, wherein said alkyl, haloalkyl, cycloalkyl, halocycloalkyl, alkenyl, alkynyl, aryl and heteroaryl groups are optionally substituted with one or more groups independently selected from the group consisting of $R_8$, $R_9$ and $R_{10}$;

$R_7$ is selected from the group consisting of H and alkyl;

$R_8$ is selected from the group consisting of —$OR_9$, —$OR_{11}$, —$SR_9$, —$SR_{11}$, —$NR_9R_{11}$, and —$NR_{11}R_{12}$;

$R_9$ is selected from the group consisting of aryl and heteroaryl, wherein said aryl and heteroaryl groups are optionally substituted with one or more groups independently selected from the group consisting of $R_{10}$ and $R_{11}$;

$R_{10}$ is selected from the group consisting of cyano, nitro, hydroxyl, halogen, alkyl, cycloalkyl, haloalkyl, alkoxy, haloalkoxy, —S(O)$_n$$R_{11}$, —S(O)$_n$$NR_{11}R_{12}$, —$NR_{11}R_{12}$, —$NR_{11}$(C=O)$R_{11}$, —$NR_{11}$(C=O)$NR_{11}R_{12}$, —$NR_{11}$S(O)$_n$$R_{11}$, —$NR_{11}$S(O)$_n$$NR_{11}R_{12}$, —C(=O)$R_{11}$, —C(=O)$OR_{11}$, —C(=O)$NR_{11}R_{12}$, —C(=S)$R_{11}$, —C(=S)$NR_{11}R_{12}$;

$R_{11}$ and $R_{12}$ are independently selected from the group consisting of hydrogen, alkyl, and haloalkyl;

$R_{13}$ and $R_{13a}$ are independently selected from the group consisting of a bond, —$NR_{11}SO_2NR_{11}$—, —$NR_{11}SO_2$—, —C(=$NR_7$)—, —C(=$NR_8$)—, —C(=O)$NR_{11}$—, —C(=S)$NR_{11}$—, —S(O)$_n$—, and —S(O)$_n$$NR_{11}$—;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(14) The compound of paragraph (11), wherein:

$R_1$ and $R_{1a}$ are independently selected from the group consisting of cyano, and —C(S)$NR_7R_{11}$;

$R_2$ and $R_{2a}$ are independently selected from the group consisting of S(O)—$R_{11}$, and 4,5-dicyanoimidazol-2-yl;

$R_3$ and $R_{3a}$ are halogen;

$R_4$ and $R_{4a}$ are haloalkyl;

Z and $Z_1$ are C—$R_3$;

$R_7$ is selected from the group consisting of H and alkyl;

$R_{11}$ and $R_{12}$ are independently selected from the group consisting of hydrogen, alkyl, and haloalkyl;

$R_{13}$ and $R_{13a}$ a bond;

L is a linker selected from the group consisting of alkyl, alkenyl, alkynyl, cycloalkyl, aryl, aryloxy aryl, heteroaryl, and any combination thereof, which may optionally contain one or more N, O, S, P, or Si atoms; and wherein said linker may optionally be substituted with one or more groups independently selected from cyano, nitro, hydroxy, halogen, O, N, S, alkyl, cycloalkyl, alkoxy, thioalkyl, oxo, oximino, and alkoxyimino; and n is independently 0, 1 or 2; or a salt thereof.

(15) The compound of paragraph (11), wherein:
$R_1$ and $R_{1a}$ are cyano;
$R_2$ and $R_{2a}$ are independently selected from the group consisting of $S(O)_nR_{11}$, and 4,5-dicyanoimidazol-2-yl;
$R_3$ and $R_{3a}$ are halogen;
$R_4$ and $R_{4a}$ are haloalkyl;
Z and $Z_1$ are C—$R_3$;
$R_{11}$ is haloalkyl;
$R_{13}$ and $R_{13a}$ are a bond;
L is alkyl or haloalkyl; and
n is 2; or
a salt thereof.
(16) A composition for treatment of animals against ectoparasites comprising the compound of any one of paragraphs 1-15 and an acceptable carrier.
(17) The composition of paragraph 16, wherein the composition is a topical, dermal or subdermal formulation.
(18) The composition of paragraph 16, wherein the composition is a microemulsion, paste, pour-on formulation, ready-to-use formulation, spot-on formulation oral solution, emulsion, injectable solution, suspension or enteric formulation.
(19) The composition of paragraph 16, further comprising an additional pesticidally active ingredient.
(20) The composition of paragraph 19, wherein the the additional pesticidally active ingredient is selected from the group consisting of arylpyrazoles, nodulisporic acid or derivatives thereof, macrocyclic lactones, formamidines, pyrethroids, insect growth regulators, benzenedisulfonamide compounds, cestodal agents, pyridylmethyl derivatives, depsipeptides and mixtures thereof.
(21) A use of the composition of any one of paragraphs 16-20 in the manufacture of a medicament for the therapeutic and/or prophylactic treatment of an animal against an ectoparasite and/or an endoparasite.
(22) The use of paragraph 21, wherein the treatment is against an ectoparasite selected from the group consisting of arthropods, acarina and mixtures thereof.
(23) The use of paragraph 21, wherein the ectoparasite is selected from the group consisting of fleas, flies, lice, mites and ticks.
(24) The use of paragraph 21, wherein the treatment is against an endoparasite.
(25) An insecticidal composition comprising a compound of any one of paragraphs 1-15 and an acceptable carrier.
(26) A use of a compound of any one of paragraphs 1-15 in the manufacture of a composition for controlling pests.
(27) A method for the preparation of pesticidal compositions, characterized in that a compound of any one of paragraphs 1-15 is mixed with extenders and/or surface-active substances.
(28) A method for controlling pests, wherein a compound of any one of paragraphs 1-15 or a composition according to paragraph 25 is allowed to act on the pests and/or their environment or on the plants, plant parts, seeds, soils, areas, materials or spaces to be kept free from them.
(29) A use of a compound of any one of paragraphs 1-15 or a composition as defined in paragraph 25 for controlling pests.
(30) A method for the treatment or prevention of a parasitic infestation or infection in an animal comprising administering an effective amount of a compound of any one of paragraphs 1-15 to the animal in need thereof.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed:
1. A compound of formula (I):

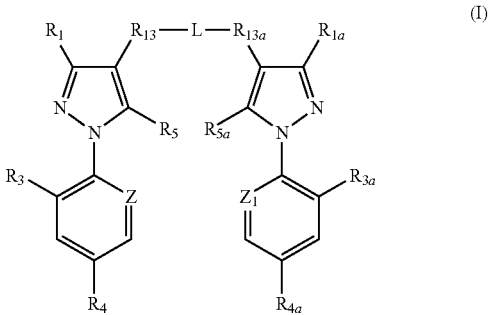

wherein:
$R_1$ and $R_{1a}$ are independently selected from the group consisting of hydrogen, cyano, halogen, —C(=O)$R_6$, —C(=O)$R_8$, —C(=O)$NR_{11}R_{12}$, —CH(=NR$_7$), —CH(=NR$_8$), —C(=NR$_7$)$R_7$, —C(=NR$_7$)$R_8$, —C(=NR$_8$)$R_7$, —C(=NNR$_7$)$R_7$, —C(=NNR$_7$)$R_8$, —C(=NNR$_8$)$R_7$, and —C(S)NR$_7$R$_{11}$;
$R_3$ and $R_{3a}$ are independently selected from the group consisting of hydrogen, halogen, cyano, nitro, alkyl, cycloalkyl, haloalkyl, alkoxy, and haloalkoxy;
$R_4$ and $R_{4a}$ are independently selected from the group consisting of halogen, cyano, nitro, $R_7$, $R_8$, —C(O)$R_{11}$, —C(=O)NR$_{11}$R$_{12}$, —C(=NR$_7$)$R_7$, —C(=NR$_7$)$R_8$, —C(=NR$_7$)NR$_{11}$R$_{12}$, —S(O)$_n$R$_{11}$, and SF$_5$;
$R_5$ and $R_{5a}$ are independently selected from the group consisting of $R_{10}$, $R_{11}$, —C(=NR$_7$)$R_7$, —C(=NR$_7$)$R_8$, —C(=NR$_8$)$R_7$, —C(=NR$_7$)NR$_{11}$R$_{12}$, —C(=S)NR$_{11}$R$_{12}$, —NR$_{11}$R$_{12}$, —NR$_{11}$C(=O)$R_8$, —NR$_{11}$C(=O)$R_{11}$, and —N=C($R_{11}$)NR$_6$;
Z and $Z_1$ are independently selected from the group consisting of nitrogen and C—$R_3$;
$R_6$ is selected from the group consisting of alkyl, haloalkyl, cycloalkyl, halocycloalkyl, alkenyl, alkynyl, aryl, and heteroaryl, wherein said alkyl, haloalkyl, cycloalkyl, halocycloalkyl, alkenyl, alkynyl, aryl, and heteroaryl groups are optionally substituted with one or more groups independently selected from the group consisting of $R_8$, $R_9$, and $R_{10}$;
$R_7$ is selected from the group consisting of hydrogen and $R_6$;
$R_8$ is selected from the group consisting of –O$R_9$, —O$R_{11}$, —S$R_9$, —S$R_{11}$, —NR$_9$R$_{11}$, and —NR$_{11}$R$_{12}$;
$R_9$ is selected from the group consisting of aryl and heteroaryl, wherein said aryl and heteroaryl groups are optionally substituted with one or more groups independently selected from the group consisting of $R_{10}$ and $R_{11}$;
$R_{10}$ is selected from the group consisting of cyano, nitro, hydroxyl, halogen, alkyl, cycloalkyl, haloalkyl, alkoxy, haloalkoxy, —S(O)$_n$R$_{11}$, —S(O)$_n$NR$_{11}$R$_{12}$, —NR$_{11}$R$_{12}$, —NR$_{11}$(C=O)$R_{11}$, —NR$_{11}$(C=O)NR$_{11}$R$_{12}$, —NR$_{11}$S(O)$_n$R$_{11}$, —NR$_{11}$S(O)$_n$NR$_{11}$R$_{12}$, —C(=O)$R_{11}$, —C(=O)O$R_{11}$, —C(=O)NR$_{11}$R$_{12}$, —C(=S)$R_{11}$, and —C(=S)NR$_{11}$R$_{12}$;
$R_{11}$ and $R_{12}$ are independently selected from the group consisting of hydrogen, alkyl, haloalkyl, cycloalkyl, halocycloalkyl, alkenyl, haloalkenyl, alkynyl, and haloalkynyl;

$R_{13}$ and $R_{13a}$ are independently selected from the group consisting of —$NR_{11}C(=S)$—, —$NR_{11}SO_2NR_{11}$, —$NR_{11}SO_2$—, —$C(=NR_7)$—, —$C(=NR_8)$—, —$C(=S)NR_{11}$—, and —$S(O)_nNR_{11}$—;

L is a linker selected from the group consisting of alkyl, alkenyl, alkynyl, cycloalkyl, aryl, aryloxy aryl, heteroaryl, and any combination thereof, which may optionally contain one or more nitrogen, oxygen, sulfur, phosphorus, or silicon atoms; and wherein said linker may optionally be substituted with one or more groups independently selected from cyano, nitro, hydroxy, halogen, oxygen, nitrogen, sulfur, alkyl, cycloalkyl, alkoxy, thioalkyl, oxo, oximino, and alkoxyimino; and n is independently 0, 1, or 2; or a salt thereof.

2. The compound of claim 1, wherein:

$R_1$ and $R_{1a}$ are independently selected from the group consisting of hydrogen, cyano, halogen, —$C(=O)R_6$, —$C(=O)R_8$, —$C(=O)NR_{11}R_{12}$, —$CH(=NR_7)$, —$CH(=NR_8)$, —$C(=NR_7)R_7$, —$C(=NR_7)R_8$, —$C(=NR_8)R_7$, and —$C(S)NR_7R_{11}$;

$R_3$ and $R_{3a}$ are independently selected from the group consisting of hydrogen, halogen, alkyl, cycloalkyl, haloalkyl, alkoxy, and haloalkoxy;

$R_4$ and $R_{4a}$ are independently selected from the group consisting of halogen, $R_7$, $R_8$, —$S(O)_nR_{11}$, and $SF_5$;

$R_5$ and $R_{5a}$ are independently selected from the group consisting of $R_{10}$, $R_{11}$, —$C(=NR_7)R_7$, —$C(=NR_7)R_8$, —$C(=NR_8)R_7$, —$C(=NR_7)NR_{11}R_{12}$, —$C(=S)NR_{11}R_{12}$, —$NR_{11}R_{12}$, and —$N=C(R_{11})NR_6$;

Z and $Z_1$ are C—$R_3$; and $R_{13}$ and $R_{13a}$ are independently selected from the group consisting of a —$C(=NR_7)$—, —$C(=NR_8)$—, —$C(=S)NR_{11}$—, and —$S(O)_nNR_{11}$—.

3. The compound of claim 1, wherein:

$R_1$ and $R_{1a}$ are independently selected from the group consisting of cyano, halogen, and —$C(S)NR_7R_{11}$;

$R_3$ and $R_{3a}$ are halogen;

$R_4$ and $R_{4a}$ are independently selected from the group consisting of halogen, haloalkyl, —$S(O)_nR_{11}$, and $SF_5$;

$R_5$ and $R_{5a}$ are independently selected from the group consisting of alkyl, haloalkyl, —$NR_{11}R_{12}$, and —$N=C(R_{11})NR_6$;

Z and $Z_1$ are C—$R_3$;

$R_7$ is selected from the group consisting of hydrogen and alkyl;

$R_{11}$ and $R_{12}$ are independently selected from the group consisting of hydrogen, alkyl, and haloalkyl; and $R_{13}$ and $R_{13a}$ are independently selected from the group consisting of a —$C(=NR_7)$—, —$C(=NR_8)$—, —$C(=S)NR_{11}$—, and —$S(O)_nNR_{11}$—.

4. The compound of claim 1, wherein:

$R_1$ and $R_{1a}$ are independently selected from the group consisting of cyano and —$C(S)NR_7R_{11}$;

$R_3$ and $R_{3a}$ are halogen;

$R_4$ and $R_{4a}$ are haloalkyl;

$R_5$ and $R_{5a}$ are independently selected from the group consisting of alkyl and —$NR_{11}R_{12}$;

Z and $Z_1$ are C—$R_3$;

$R_7$ is selected from the group consisting of hydrogen and alkyl;

$R_{11}$ and $R_{12}$ are hydrogen; and $R_{13}$ and $R_{13a}$ are —$S(O)_nNR_{11}$.

5. The compound of claim 1, wherein:

$R_1$ and $R_{1a}$ are cyano;

$R_3$ and $R_{3a}$ are halogen;

$R_4$ and $R_{4a}$ are haloalkyl;

$R_5$ and $R_{5a}$ are independently selected from the group consisting of alkyl and —$NR_{11}R_{12}$;

Z and $Z_1$ are C—$R_3$;

$R_{11}$ and $R_{12}$ are hydrogen;

$R_{13}$ and $R_{13a}$ are —$S(O)_nNR_{11}$—;

L is alkyl or haloalkyl; and n is 2.

6. A composition comprising: (A) an effective amount of the compound of claim 1 to treat or prevent a parasite infestation or infection in an animal; and (B) a veterinarily acceptable carrier.

7. The composition of claim 6, wherein the composition is a topical, dermal, or subdermal formulation.

8. The composition of claim 6, wherein the composition is a microemulsion, a paste, a pour-on formulation, a ready-to-use formulation, a spot-on formulation, an oral solution, an emulsion, an injectable solution, a suspension, or an enteric formulation.

9. The composition of claim 6, further comprising an additional pesticidally active ingredient.

10. The composition of claim 9, wherein the additional pesticidally active ingredient is selected from the group consisting of arylpyrazoles, nodulisporic acid or derivatives thereof, macrocyclic lactones, formamidines, pyrethroids, insect growth regulators, benzenedisulfonamide compounds, anti-cestodal agents, pyridylmethyl derivatives, depsipeptides, and mixtures thereof.

11. An insecticidal composition comprising: (A) an effective amount of the compound of claim 1 to treat or prevent an insect infestation or infection in an animal; and (B) an acceptable carrier.

12. A method for the preparation of pesticidal compositions, comprising mixing an effective amount of the compound of claim 1 to treat or prevent an insect infestation or infection in an animal with extenders or surface-active substances.

13. A method of controlling pests, comprising applying an effective amount of the compound of claim 1 to treat or prevent an insect infestation or infection in an animal to the pests or their environment, or on the plants, plant parts, seeds, soils, areas, materials, or spaces to be kept free from them.

14. A method for the treatment or prevention of a parasitic infestation or infestation in an animal comprising administering an effective amount of the compound of claim 1 to treat or prevent an insect infestation or infection in an animal to the animal in need thereof.

\* \* \* \* \*